(12) United States Patent
Cheng et al.

(10) Patent No.: US 7,160,931 B2
(45) Date of Patent: Jan. 9, 2007

(54) THERMALLY REVERSIBLE IMPLANT AND FILLER

(76) Inventors: Yu-Ling Cheng, 1379 Glenburnie Road, Mississauga, Ontario (CA) L5G 3C7; Michael H. May, 9 Terrance Dr., Brantford, Ontario (CA) N3R 3G2; John L. Semple, 63 Kingswood Road, Toronto, Ontario (CA) M4E 3N4; Hai-Hui Lin, 3819 Parkwood Ct., Loveland, OH (US) 45140

( * ) Notice: Subject to any disclaimer, the term of this patent is extended or adjusted under 35 U.S.C. 154(b) by 441 days.

(21) Appl. No.: 10/428,520

(22) Filed: May 2, 2003

(65) Prior Publication Data

US 2004/0029994 A1 Feb. 12, 2004

Related U.S. Application Data

(63) Continuation-in-part of application No. 10/221,084, filed as application No. PCT/CA01/00325 on Mar. 15, 2001.

(60) Provisional application No. 60/189,489, filed on Mar. 15, 2000.

(51) Int. Cl.
*A61F 2/00* (2006.01)
*C08L 51/00* (2006.01)
*C08L 53/00* (2006.01)

(52) U.S. Cl. .................. 523/113; 524/504; 524/505; 424/422

(58) Field of Classification Search ............... 523/113; 524/504, 505
See application file for complete search history.

(56) References Cited

U.S. PATENT DOCUMENTS

| | | | | |
|---|---|---|---|---|
| 4,454,110 | A | * | 6/1984 | Caslavsky et al. ............ 424/54 |
| 4,917,892 | A | * | 4/1990 | Speaker et al. ............. 424/401 |
| 4,938,763 | A | | 7/1990 | Dunn et al. .............. 604/891.1 |
| 5,278,201 | A | | 1/1994 | Dunn et al. ................. 523/113 |
| 5,278,204 | A | | 1/1994 | Tojo et al. .................. 523/212 |
| 5,340,849 | A | | 8/1994 | Dunn et al. ................. 523/113 |
| 5,410,016 | A | | 4/1995 | Hubbell et al. ............. 528/354 |
| 5,688,855 | A | | 11/1997 | Stoy et al. .................. 524/505 |
| 5,702,717 | A | | 12/1997 | Cha et al. ................... 424/425 |
| 5,733,950 | A | | 3/1998 | Dunn et al. ................. 523/113 |
| 5,739,176 | A | | 4/1998 | Dunn et al. ................. 523/113 |
| 5,744,153 | A | | 4/1998 | Yewey et al. ............... 424/426 |
| 5,759,563 | A | | 6/1998 | Yewey et al. ............... 424/426 |
| 6,201,065 | B1 | * | 3/2001 | Pathak et al. ................. 525/90 |
| 6,350,812 | B1 | | 2/2002 | Vert et al. ................... 524/845 |

FOREIGN PATENT DOCUMENTS

| | | |
|---|---|---|
| FR | 2 741 628 | 5/1997 |
| JP | 11169703 | 6/1999 |
| WO | WO 94/05342 | 3/1994 |
| WO | WO 95/24430 | 9/1995 |
| WO | WO 97/05185 | 2/1997 |
| WO | WO 99/07343 | 2/1999 |
| WO | WO 00/00222 | 1/2000 |
| WO | WO 00/45868 | 8/2000 |
| WO | WO 00/69942 | 11/2000 |
| WO | WO 01/68768 | 9/2001 |

OTHER PUBLICATIONS

Nagahara et al., "Hydrogel Formation Via Hybridization of Oligonucleotides Derivatized in Water-Soluble Vinyl Polymers," *Polymer Gels and Networks*, 4: 111-127, (1996).
Miyata et al., "Preparation of an Antigen-Sensitive Hydrogel Using Antigen-Antibody Bindings," *Macromolecules*, 32: 2082-2084, (1999).
Miyata et al., "A Reversibly Antigen-Responsive Hydrogel," *Nature*, 399: 6738, 766-769, (1999).
Petka et al., "Reversible Hydrogels from Self-Assembling Artificial Proteins," *Science*, 281: 5375, 389-392, (1998).
Cabana et al., "Study of the Gelation Process of Polyethylene Oxide$_a$-Polypropylene Oxide$_b$-Polyethylene Oxide$_a$ Copolymer (Poloxamer 407) Aqueous Solutions," *Journal of Colloid and Interface Science*, 190, 307-312 (1997).
Jeong et al., "New Biodegradable Polymers for Injectale Drug Delivery Systems," *Journal of Controlled Release*, 62, 109-114 (1999).
Jeong et al., "Thermoreversible Gelation of PEG-PLGA-PEG Triblock Copolymer Aqueous Solutions," *Macromolecules*, 32: 7064-7069, (1999).
Jeong et al., "Biodegradable Block Copolymers as Injectable Drug-Delivery Systems," *Nature*, 388: 6645, 860-862, (1997).

(Continued)

*Primary Examiner*—Tae H. Yoon
(74) *Attorney, Agent, or Firm*—Thomas M. Saunders; Brown Rudnick Berlack Israels LLP

(57) ABSTRACT

The invention relates to the use of a thermal reversible gel, such as a copolymer composition, as a biological filler or implant. The gel has a semi-solid form at body temperature, but upon cooling to a temperature below a threshold level, the gel is liquefied and can be re-shaped, re-sized, manipulated or removed from the body. The gel may be used as a subcutaneous implant, a biological filler, joint or tissue spacer, for wrinkle filling or other cosmetic implants, as a soft-tissue replacement for reconstructive surgery, or as a barrier within the lumen of a biological structure, such as a blood vessel. The implant may be used to provide reversible birth control by providing, for example, a reversible barrier to the cervix or a reversible blockage of the lumen of the vas deferens.

14 Claims, 8 Drawing Sheets

OTHER PUBLICATIONS

Capello et al., "In-Situ Self-Assembling Protein Polymer Gel Systems for Administration, Delivery, and Release of Drugs," *Journal of Controlled Release*, 53, 105-117, (1998).

Yoshioka et al., "Preparation of Poly (N-Isopropylacrylamide)-*b*-Poly(Ethylene Glycol) And Calorimetric Analysis of its Aqueous Solution," *J.M.S. Pure Appl. Chem.*, A31: (1) 109-112, (1994).

Yoshioka et al., "A Synthetic Hydrogel With Thermoreversible Gelation. I. Preparation And Rheological Properties," *J.M.S. Pure Appl. Chem.*, A31: (1) 113-120, (1994).

Yoshioka et al., "A Synthetic Hydrogel With Thermoreversible Gelation. II..Effect of Added Salts," *J.M.S. Pure Appl. Chem.*, A31: (1) 121-125, (1994).

Kaneko et al., "Rapid Deswelling Response of Poly(N-isopropylacrylamide) Hydrogels by the Formation of Water Release Channels Using Poly (ethylene oxide) Graft Chains," *Macromolecules*, 31: 6099-6105, (1998).

Topp et al., "Thermosensitive Micelle-Forming Block Copolymers of Poly (ethylene glycol) and Poly (N-isopropylacrylamide)," *Macromolecules*, 30: 8518-8520, (1997).

Virtanen et al., "Grafting of Poly (N-isopropylacrylamide) with Poly(ethylene oxide) under Various Reaction Conditions," *Macromolecules*, 33: 336-341, (2000).

Newman et al., "Reversible Association of Cellulose Nitrate in Ethanol," *Journal of Physical Chemistry*, 60: 648-656, (1956).

Kudaibergenov et al., "Temperature-Responsive Swelling and Deswelling of the Copolymers From Vinyl Ether of Ethylene Glycol and Butyl Vinyl Ether," *Macromol. Rapid Commun.* 16, 855-860, (1995).

Zhongli et al., "A Study on the Deswelling Behaviour of a Thermo-Responsive Hydrogel Prepared by Radiation Polymerization," *Radiat. Phys. Chem.*, 42, Nos. 4-6, 959-962, (1993).

Nishimura et al., "Temperature-Responsive Hydrogels from Cellulose," *Macromol. Symp.*, 120: 303-313, (1997).

Sarkar, "Thermal Gelation Properties of Methyl and Hydroxypropyl Methylcellulose," *Journal of Applied Polymer Science*, 24: 1073-1087, (1979).

Hvidt et al., "Micellization and Gelation of Aqueous Solutions of a Triblock Copolymer Studied by Rheological Techniques and Scanning Calorimetry," *Journal of Physical Chemistry*, 98: 12320-12328, (1994).

Almgren et al., "Self-Aggregation and Phase Behavior of Poly(ethylene oxide)-Poly(propylene oxide)-Poly(ethylene oxide) Block Copolymers in Aqueous Solution," *Colloid Polymer Science*, 273: 2-15, (1995).

\* cited by examiner

B—C—A—C—B

A

B

A

B

A

B (a) AB (b) A(B)$_2$ (c) A(B)$_4$ (d) A(B)$_8$ $C_{min}$ is the minimum gelation concentration, below which no gel forms

THERMALLY REVERSIBLE IMPLANT AND FILLER

CROSS REFERENCE TO RELATED APPLICATIONS

This application is a Continuation-In-Part of and claims priority to U.S. patent application Ser. No. 10/221,084, filed Jun. 9, 2003 which was filed on the basis of as PCT/CA01/00325 (filed Mar. 15, 2001), hereby incorporated by reference. Further, this application is entitled to the benefit of and claims priority from U.S. Provisional Patent Application No. 60/189,489, filed Mar. 15, 2000, which is hereby incorporated by reference.

FIELD OF THE INVENTION

The present invention relates generally to thermally reversible polymer implants and fillers for use in biological applications.

BACKGROUND OF THE INVENTION

Prior art implants and fillers for use in biological applications generally do not allow thermally reversible removal or modification of the substance used. For example, the use of silicone implants and polymeric implants do not allow easy modification of shape, volume or placement in a reversible way, once the implant is in place.

In reconstructive and cosmetic surgery and other cosmetic procedures, the success or failure of the procedure depends in part on the satisfaction of the patient with the appearance of their altered physical attribute. There are very few methods available, short of a subsequent surgery or repeat procedures, to correct errors or affect changes to a cosmetic alteration.

With an aging population and a concurrent emphasis on youthful appearance, a number of methods have arisen for reducing facial lines and wrinkles. One such method involves injection of a toxin below the skin to cause a localized immune reaction that smoothes out wrinkles. One problem with this method is the potential or perceived danger to the patient due to unexpected reactions to the toxin. Other methods involve injection of natural materials (e.g., collagen and hyaluronic acid) under the wrinkle to raise the skin. One problem with these implants is the potential or perceived danger that these materials may be immunogenic, be allergenic or carry animal-borne diseases (e.g., mad cow disease or its human equivalent—Creutzfeldt-Jacob Disease). In addition, these implants begin to degrade upon implantation, making it difficult or impossible to remove them, if necessary. In some cases, small, non-degradable beads (e.g., polymethymethacrylate) are suspended in wrinkle fillers to give them a longer-lasting effect. These small beads become surrounded by fibrous tissue as part of the normal foreign body reaction to implants, which prolongs their effect, but makes them impossible to remove, if desired.

Current methods of birth control are either irreversible, or only reversible through lengthy surgical procedures (for example, a reverse vasectomy). Other methods, such as "the pill" use pharmaceutical means to cause a temporarily infertile state. Subject compliance is necessary for the success of such methods. There is a need for reversible long-term options for birth control for both men and women.

Block and graft copolymers are used for a variety of physiological and industrial applications. The solubility of a copolymer in a particular solvent depends inter alia on the characteristics of the monomeric components incorporated into the copolymer.

Polymers capable of gelation induced by environment changes are known. Solvent-induced gelation has also been exploited as a mechanism for producing in situ gelable materials. The solvent-induced gelation concept employs a polymer that is soluble in a non-aqueous solvent, but insoluble in water. When a non-aqueous solution of such a polymer is injected into an aqueous environment, the non-aqueous solvent is exchanged for water and the polymer precipitates, forming a solid mass in situ. Solvent-induced gelation systems have the disadvantage that the initial fluid form of the polymer is formed in a solvent other than the solvent in which the gel eventually forms. U.S. Pat. No. 5,744,153 (Apr. 28, 1998) and No. 5,759,563 (Jun. 2, 1998), both to Yewey et al., describe a composition for in situ formation of a controlled drug release implant based on the solvent-induced gelation concept.

A series of patents to Dunn et al. also describe a solvent-induced gel composition (U.S. Pat. No. 5,739,176 issued Apr. 14, 1998; U.S. Pat. No. 5,733,950 issued Mar. 31, 1998; U.S. Pat. No. 5,340,849 issued Aug. 23, 1994; U.S. Pat. Nos. 5,278,201 and 5,278,204 both issued Jan. 11, 1994; and U.S. Pat. No. 4,938,763 issued Jul. 3, 1990). The composition includes a water-insoluble polymer and a drug solubilized in an organic solvent carrier. When the composition is injected into a physiological (aqueous) environment, such as a human subject, the polymer precipitates to form a solid mass. Solvent-induced gel compositions have the disadvantage that an organic solvent is injected into a subject merely to carry the polymer and drug in a liquid form. Thus, the organic solvent must subsequently be metabolized or cleared by the body.

Self-assembling hydrogels have been receiving increasing attention in the last few years, both for their intrinsic scientific interest, and for their potential clinical and non-clinical applications. A number of elegant mechanisms for self-assembling hydrogels have been proposed. Nagahara et al. showed that gels can be formed by complexation between complementary oligonucleotides grafted onto hydrophilic polymers (Polymer Gels and Networks, 4:(2) 111–127, 1996). Miyata et al. prepared antigen sensitive hydrogels based on antigen-antibody binding (Miyata et al., Macromolecules, 32: (6) 2082–2084, 1999; Miyata, Nature, 399: (6738) 766–769, 1999). Petka et al. illustrated a gelation mechanism using triblock copolymers containing a central hydrophilic core and terminal leucine zipper peptide domains (Science, 281: (5375) 389–392, 1998). The terminal domains form coil-coil dimers or higher order aggregates to provide crosslinking when cooled from above its pH-dependent melting point. Thermoreversibility was demonstrated with some hysteresis due to the slow kinetics of coil-coil interactions.

Triblock copolymers having a central hydrophobic poly (propylene oxide) (PPO) segment and hydrophilic poly (ethylene oxide) (PEO) segments attached at each end are commercially available. The aqueous solution of these triblock copolymers (PEO-PPO-PEO) have a fluid consistency at room temperature, and turn into weak gels when warmed to body temperature by forming oil-in-water micelles in aqueous solution. The gelation of the polymer is believed to occur via the aggregation of the micelles (Cabana, et al., J. Coll. Int. Sci., 190(1997) 307).

A group led by S. W. Kim have reported the development of thermosensitive biodegradable hydrogels (Jeong et al., J. Controlled Release, 62 (1999) 109–114; Jeong et al., Macromolecules, 32: (21) 7064–7069, 1999; Jeong et al., Nature, 388 (1997) 860–862). These hydrogels are block copolymers of PEO and poly(L-lactic acid) (PLLA) in either a di-block architecture PEO-PLLA, or a tri-block architecture PEO-PLLA-PEO. They also report triblock copolymers of poly(ethylene oxide) and poly(lactide-co-glycolide) (PLGA) having the architecture PEO-PLGA-PEO. Aqueous solutions of these polymers were reported to undergo temperature-sensitive phase transitions between fluid solution and gel phases. In aqueous solution, these polymers form micelles composed of hydrophobic cores (either PLGA or PLLA) and hydrophilic surfaces (PEO). Gelation is believed to be due to the aggregation of micelles driven by hydrophobic interactions. This group has also discussed the synthesis of PEO copolymers in multi-armed star shaped architectures having polycaprolactone (PCL) or PLLA chains attached to the PEO arms.

Another class of in situ gelable materials is based on polymers made from proteins, or "protein polymers". Cappello, et al. (J Controlled Release 53 (1998) 105–117) reported gelforming block copolymers based on repeating amino acid sequences from silk and elastin proteins. When heated to body temperature, the proteins self-assemble via a hydrogen bond mediated chain crystallization mechanism to form an irreversible gel. The gelation occurs over a relatively long time period of more than 25 minutes.

Although a variety of gelling or precipitatable polyethylene glycol/poly(N-isopropylacrylamide) copolymers have been synthesized, none was designed and synthesized with in situ gelation applications in mind. See, for example Yoshioka et al., J. M. S Pure Appl. Chem., A31: (1) 109–112, 1994; Yoshioka, J. M. S. Pure Appl. Chem., A31: (1) 113–120, 1994; Yoshioka, J. M. S Pure Appl. Chem., A31: (1) 121–125, 1994; Kaneko, Macromolecules, 31: 6099–6105, 1998; Topp, et al., Macromolecules, 30: 8518–8520, 1997; and Virtanen, Macromolecules, 33: 336–341, 2000.

Topp et al. disclose block copolymers of PEG and PNIPAAm having the structure of either PNIPAAm-PEG or PNIPAAm-PEG-PNIPAAM which form spherical micelles in aqueous solution (Macromolecules, 30: 8518–8520, 1997). The block copolymers were synthesized by the $Ce^{+4}$ initiated attachment of NIPAAm monomers onto the hydroxyl terminals of PEG chains. It was shown that as PNIPAAm segments grew in length during synthesis, micelles having a PNIPAAm core and PEG corona were formed, and the polymerization of PNIPAAm chains continued in the core of the micelles. The copolymers formed by Topp et al. are of a form appropriate for use in a surfactant composition for drug loaded micelles. However, micelles are isolated entities having no load bearing characteristics, do not form gels, and the formation of micelles is associated with a dilute solution state.

The block copolymers formed by Topp et al. consisted of compositions with PNIPAAm to PEG mass ratios ($M_{n,PNIPAAm}/M_{n,PEG}$) ranging from about 0.14 to 0.48, and they found that block copolymers with a $M_{n,PNIPAAm}/M_{n,PEG}$ ratio exceeding ⅓ show aggregation in water at temperatures below the lower critical solution temperature (LCST) at which a solubility change occurs, and thus are less useful for micelle formation than copolymers with ratios less than ⅓.

There is a need for a gelable polymer that is responsive to environmental changes other than solvent exchange. Further, there is a need for a gelable polymer composition capable of reversibly forming a strong gel.

SUMMARY OF THE INVENTION

It is an object of the present invention to provide a biological implant that is thermally reversible so that it may be cooled for easier removal from the site of implantation. Further, it is an object of the invention to obviate or mitigate at least one disadvantage of previous implants.

The invention provides a thermally reversible biological implant comprising a copolymer and an aqueous solvent, the copolymer having the structure A(B)n, wherein A is soluble in the solvent, B is convertible from soluble to insoluble when heated to a temperature between ambient temperature and body temperature, and n is greater than 1, the implant being convertible from liquid to semi-solid when B is insoluble. According to certain embodiments, n may optionally be greater than 2, or may range from 2 to 8.

Further, the invention provides a method of forming a removable implant in an animal comprising inserting a thermally reversible gel into said animal, said gel having a semi-solid form at body temperature and a liquid form upon cooling to a temperature below a threshold temperature, said threshold temperature being at least 5° C. below body temperature.

Additionally, the invention provides a method of forming an in situ implant or an implant in vitro comprising the steps of (i) forming a gelable composition comprising a copolymer and an aqueous solvent, the copolymer having the structure A(B)n. "A" is soluble in the solvent, while "B" is convertible from soluble to insoluble when heated to a temperature between ambient temperature and body temperature, and n is greater than 1. The composition being convertible from liquid to gel when B is insoluble. The step of (ii) inserting said composition into a subject to form an in situ implant or heating said composition to at least said gelling temperature to form an in vitro implant is then conducted.

Further, the invention relates to a process for preparing a thermally reversible gel by reacting PEG and NiPAAm at a temperature of about 50° C. in the presence of ceric ammonium nitrate in nitric acid to form a gel. Optionally, the process may additionally comprise purification of the gel formed by incubating the gel in warm water at low concentration, filtering the gel, and rinsing the gel with warm water. The thermally reversible gel so formed is also within the scope of the invention.

Other aspects and features of the present invention will become apparent to those skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

temperature sweep of oscillatory measurement, occurs at a temperature between the onset and peak of the endotherm as detected by (B) DSC temperature scan.

Figure 5:
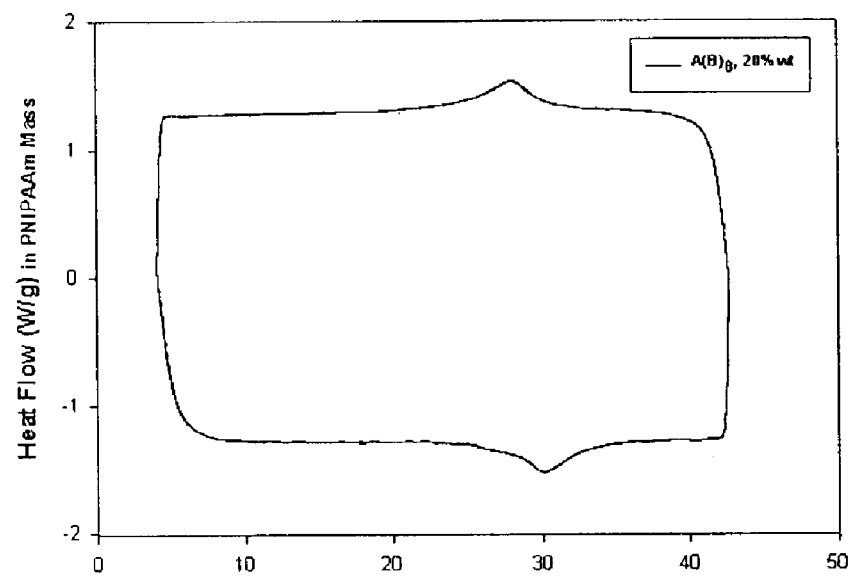
Figure 5:
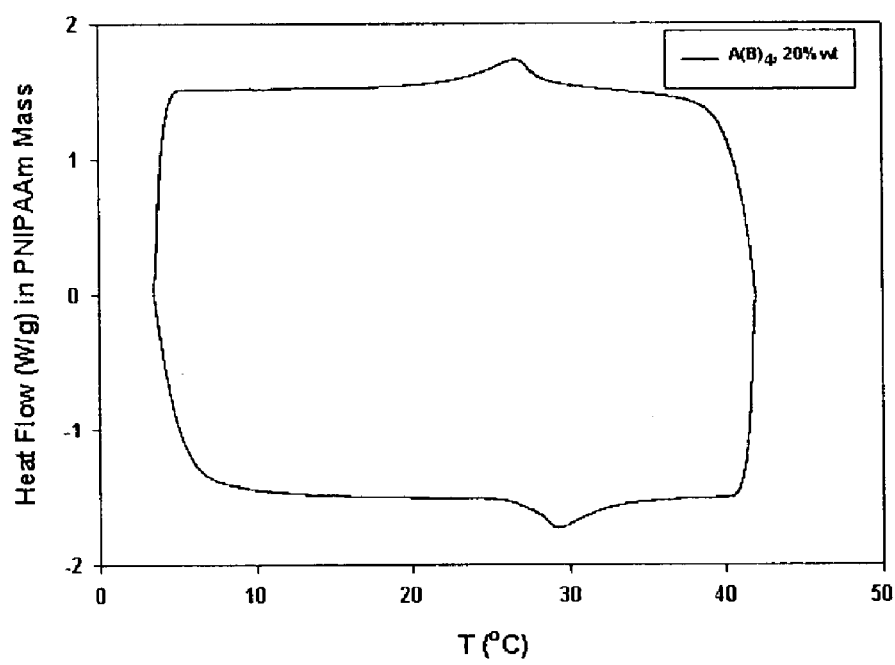

FIG. 5 shows the superposition of the DSC scans for multiple cycles for both (A) the four-arm polymer $A(B)_4$ and (B) the eight-arm polymer $A(B)_8$, both at 20% wt in water (2° C./min for 30 cycles), illustrating the full thermal reversibility of copolymers according to an embodiment of the invention.

Figure 6:
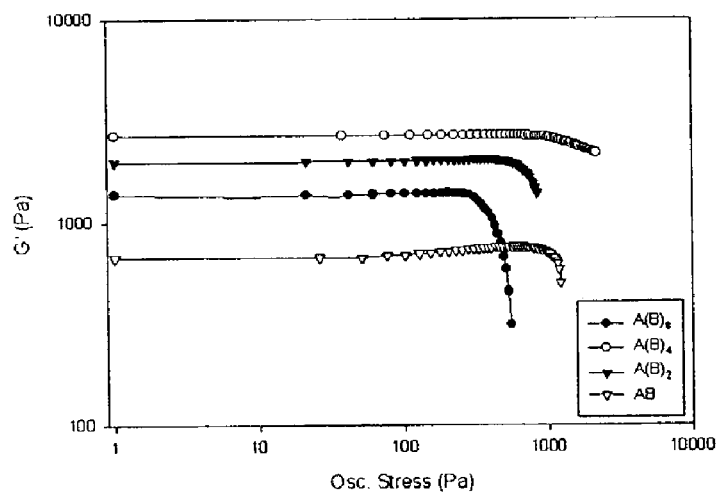
Figure 6:
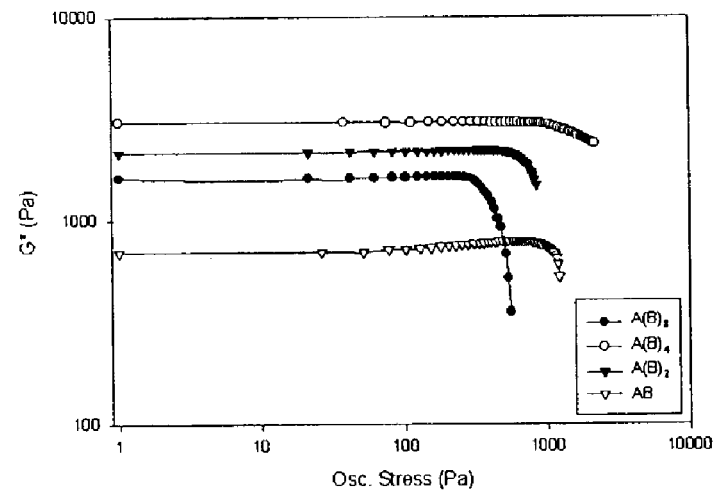
Figure 6:
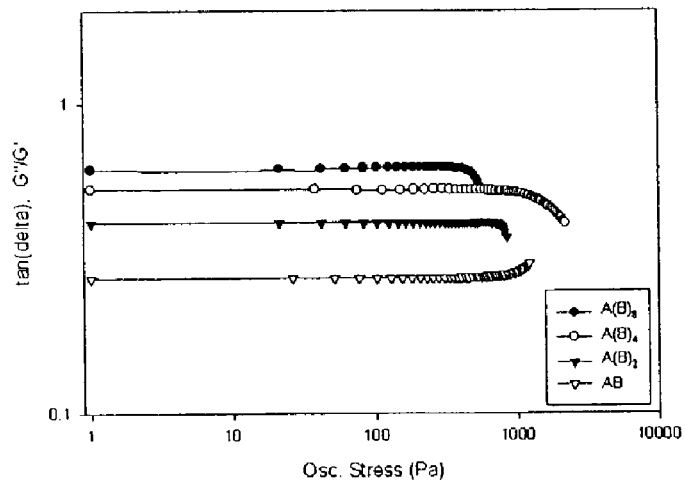

FIG. 6 illustrates parameters relating to the Theological behavior of copolymers. (A) Elastic Modulus vs. Oscillatory Stress; (B) Overall Modulus vs. Oscillatory Stress; and (C) tan delta vs. Oscillatory Stress. The tests were conducted at a frequency of 1 Hz.

Figure 7:
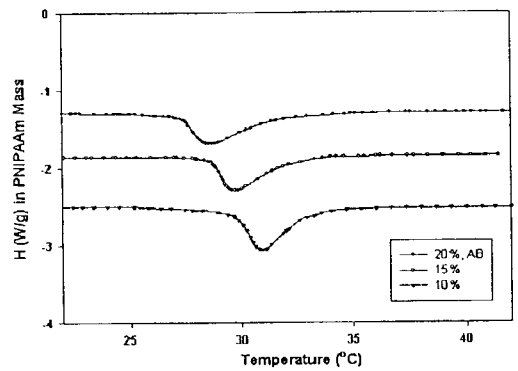
Figure 7:
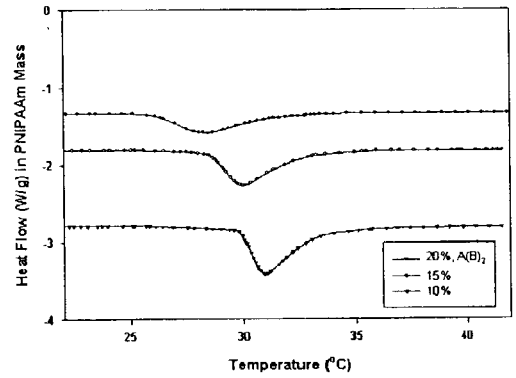
Figure 7:
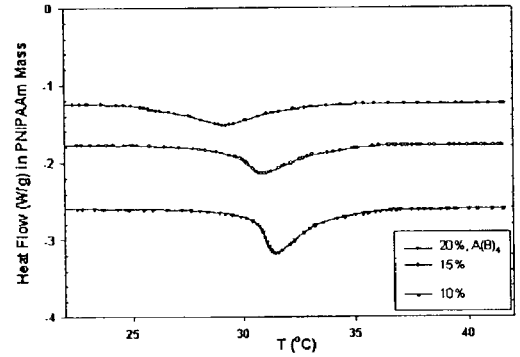
Figure 7:
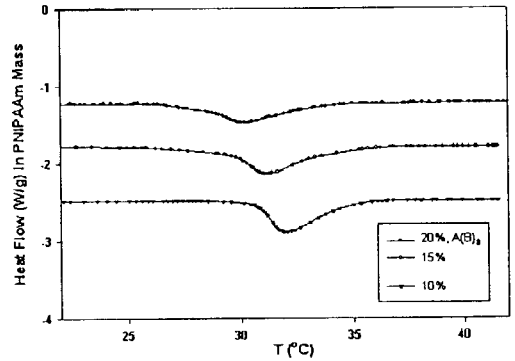

FIG. 7 illustrates thermal transition (DSC scans) of compositions containing 50/50 copolymers of PEG/PNIPAAm according to the invention at various concentrations. Comparative example (a) AB is shown relative to the inventive compositions containing (b) copolymer $A(B)_2$, (c) copolymer $A(B)_4$ and (d) copolymer $A(B)_8$.

Figure 8:
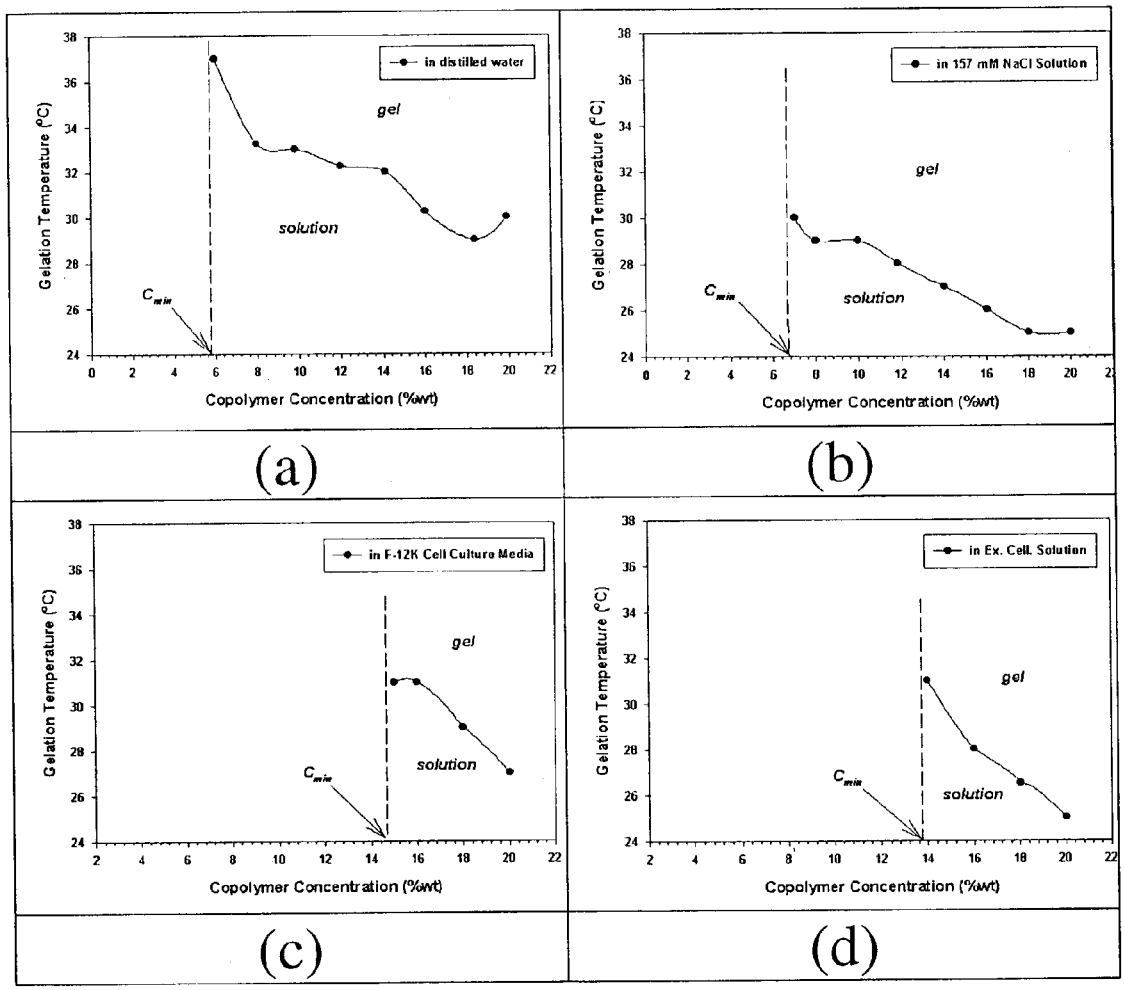

FIG. 8 provides phase diagrams PEG-PNIPAAm copolymers in (a) distilled water, (b) 157 mM NaCl solution, (c) F-12K cell culture media, and (d) extra cellular solution. $C_{min}$ is the minimum gelation concentration, below which no gel forms over the range of temperatures investigated.

Figure 9:
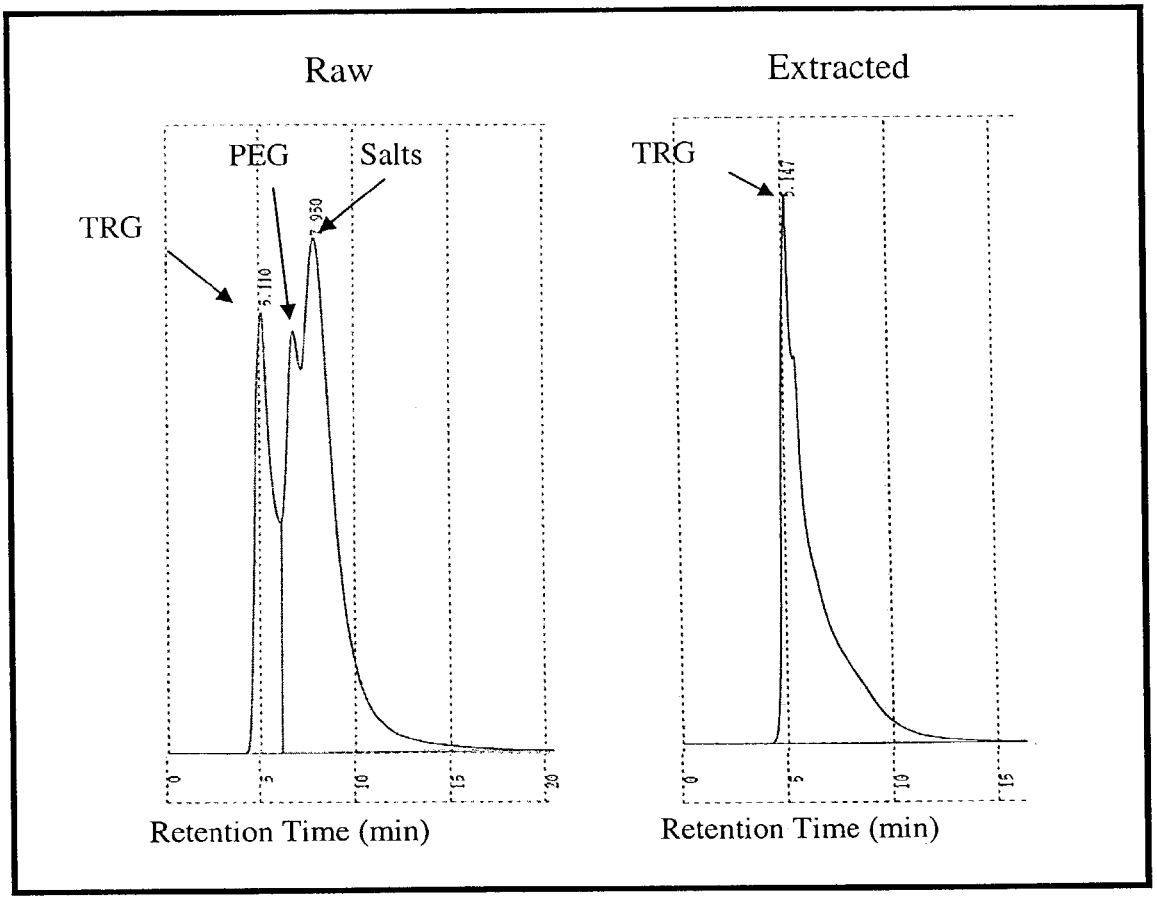

FIG. 9 illustrates gel permeation chromatograms (GPC) of raw and extracted thermoreversible gel (TRG) according to an embodiment of the invention described in Example 11.

DETAILED DESCRIPTION

The invention provides a thermally reversible biological implant comprising a copolymer and an aqueous solvent. The copolymer having the structure A(B)n, wherein A is soluble in the solvent, B is convertible from soluble to insoluble when heated to a temperature between ambient temperature and body temperature, and n is greater than 1, the implant being convertible from liquid to semi-solid when B is insoluble.

The implant can be used as a wrinkle filler, a tissue expander, a joint spacer, a tissue spacer, a vessel blocker, a cosmetic enhancer, or a breast implant filler, among a variety of other uses. In this way, the invention can also be said to relate to a method of forming such an implant or filler.

As a wrinkle filler, the implant can be injected or otherwise placed subcutaneously in a liquid form, and the body temperature allows gelling to occur. In this way, the filler advantageously can be shaped or spread thinly to achieve the desired effect while still in a liquid form. Similarly, for cosmetic or reconstructive surgery applications, the filler can be applied to a selected area of the body in a liquid form (or can be formed prior to insertion as described herein), and can be manipulated into the desired shape or to fill a desired volume. The invention has the advantage that if a subject is not happy with the results of the application, the effect can be changed and manipulated by application of cold directly to the region of the implant, provided that the threshold temperature is achieved by the implant. Reconstructive surgery or aesthetic enhancement may incorporate the filler or implant of the invention. Regions of the face, such as cheeks, nose, eyes, and ears (soft tissue) can be reconstructively augmented or enhanced using the invention.

As a joint spacer, the thermally reversible filler can be used to keep the components of joints spaced apart, such as in the knee or in vertebrae. The joint spacer may be used as an intervening layer as needed, such as when an individual is awaiting knee or back surgery. For example, if cartilage is degraded, the filler may be used in its place. Further, if a meniscus that caps a joint is damaged or degraded, the filler may be used as a replacement. The filler can be considered an artificial disc, when vertebrae are damaged or degraded. The advantage of the filler in this use is that it is injectable, moldable, and ultimately removable. Thus, if an individual is awaiting surgery, such as knee replacement surgery, the filler can be injected in a minimally invasive manner and removed once the replacement joint is ready, or the surgery is complete.

As a tissue spacer, the filler can be used in a manner which is generally similar to the above-noted joint spacer. However, the tissues to be separated need not be joints, but any tissues requiring spaced proximity to each other can be separated with the filler. The implant can be used in a similar manner to fill a cavity. In a region of the body where tissue has been removed, the implant may be inserted in order to conserve the normal appearance of that tissue, or to protect the underlying area. As an example of this, injury or trauma to the eye may benefit from use of the filler. In such instances in which the filler is used as a tissue spacer, the implant can also be removed in stages or re-shaped, so that it is not all removed at the same time, if the spacing requirements of the tissue change over time.

For breast augmentation or reconstruction, the thermally reversible filler can be used as an alternative to silicone or saline as fillers of breast implants, and advantageously can achieve a high viscosity once the gel is thermally formed in a semi-solid state. The shape and size of the breast implant can be varied by exploiting the thermal reversibility of the filler. Augmentation or reconstruction of other body areas also falls within the scope of the invention.

The thermally reversible implant or filler of the invention can be used as a temporary sealant in surgical procedures, for example as an option to severing or cauterizing blood vessels. A blood vessel may be sealed by injection or insertion of the implant within the lumen of the vessel or by covering an area of bleeding tissue.

The thermally reversible filler can be used to block blood flow. For example, to seal the blood flow feeding a tumor, injection of the implant in liquid form into that vessel can be affected. This effect would be reversible through cooling. The invention can be applied for any number of surgical applications in which it is it is desirable to restrict or redirect blood flow, advantageously in a reversible way.

In instances where damage has been done to certain structural components of the body, the implant may be used as support for that organ or tissue, or as a bulking agent or tissue expander to provide structural integrity to the tissue or surrounding area. For example, if there is damage to a biological conduit, such as the uretor, or a sphincter, such as of the bladder, the implant may be used to alter the shape or to surround that particular tissue to help it maintain the desired shape required for proper function. This may be done by inserting the implant into the tissue of interest or by forming an implant to surround or abut the tissue of interest to achieve the required outcome.

Further, the implant can be used for reversible birth control applications in both women and men. For example, in men the implant may be used for implantation within the vas deferens to cause blockage thereof. This blockage can be reversed by cooling the area to a temperature below which the implant becomes liquid, so that the blockage can be removed. In women, the implant can be applied or implanted as a cervical sealant so as to prevent conception. By cooling the area of application to a temperature below which the implant becomes liquid, the sealant is removed. In both cases, only minorly invasive methods are required for both application and removal of the implant. In this way, the invention can be said to relate to a method of forming a reversible birth control implant.

The invention relates to a method of forming a removable implant in an animal comprising inserting a thermal reversible gel into said animal, said gel having a semi-solid form at body temperature and a liquid form upon cooling to a temperature below a threshold temperature, said threshold temperature being at least 5° C. below body temperature.

The threshold temperature may differ depending on the nature of the gel or polymer used. Ideally, the threshold temperature is 5 to 15° C. below body temperature, and in this way, cooling need only be applied locally to achieve the appropriate temperature differential to cause liquefaction of the gel or polymer. Removal is then affected by any acceptable means, such as through aspiration, washing or dabbing the liquid from the area. Once the temperature of the gel from which the implant is formed is below the threshold temperature, it is liquefied, re-shapable, or removable.

The method of the invention can be said to further involve the step of removing the implant by cooling the body in the region of the implant to a temperature below the threshold temperature and extracting the implant. Also, the implant can be re-shaped by using the step of cooling the body in the region of the implant below the threshold temperature, re-shaping or re-sizing the implant in the liquid state and then forming a solid gel again of the new shape and volume.

The invention also relates to a method of forming an in situ implant or an implant in vitro. This method comprises formation of a gelable composition comprising a copolymer and an aqueous solvent, the copolymer having the structure A(B)n. "A" is soluble in the solvent and "B" is convertible from soluble to insoluble when heated to a temperature between ambient temperature and body temperature, and n is greater than 1. For example, n may be an integer from 2 to 8. The gelable composition is convertible from liquid to gel when B is insoluble, and those conditions involve increasing the temperature to body temperature after the gel is inserted into the per-determined portion of the body. The subsequent step of inserting the composition into a subject to form an in situ implant may be used, or alternatively, the step of heating the composition to at least the gelling temperature (about body temperature) to form an in vitro implant can then be used.

Although a variety of thermal reversible gelling substances can be used, and the invention is not intended to be limited to any specific composition, the embodiments of a gelable copolymer described herein are exemplary substances from which the instant implant or filler may be formed.

According to one embodiment of the invention, the implant is formed of a getable copolymer responsive to temperature changes in the environment. A copolymer composition that undergoes structural changes in response to changes in the environment may be used. Within the composition, the copolymer undergoes a phase transition from liquid to gel in response to changes in an environmental parameter such as, for example temperature, pH, ionic strength of the composition, or combinations of these parameters.

The mechanism of environment responsive gel formation according to the invention has not been observed or described previously. The inventive polymer A(B)n undergoes gel formation under specific environmental conditions as a result of environment-sensitive aggregation of the arms (B) of the copolymer. The aggregates of arms (B) thus form physical crosslinks between the core component (A) of the copolymers to create the gel structure when the environmental conditions are those under which the arm component (B) is insoluble. The copolymer composition readily converts between a liquid state (when solubilized either in aqueous or non-aqueous solvents) and a gel state when subjected to changes in the environmental conditions.

Figure 1:
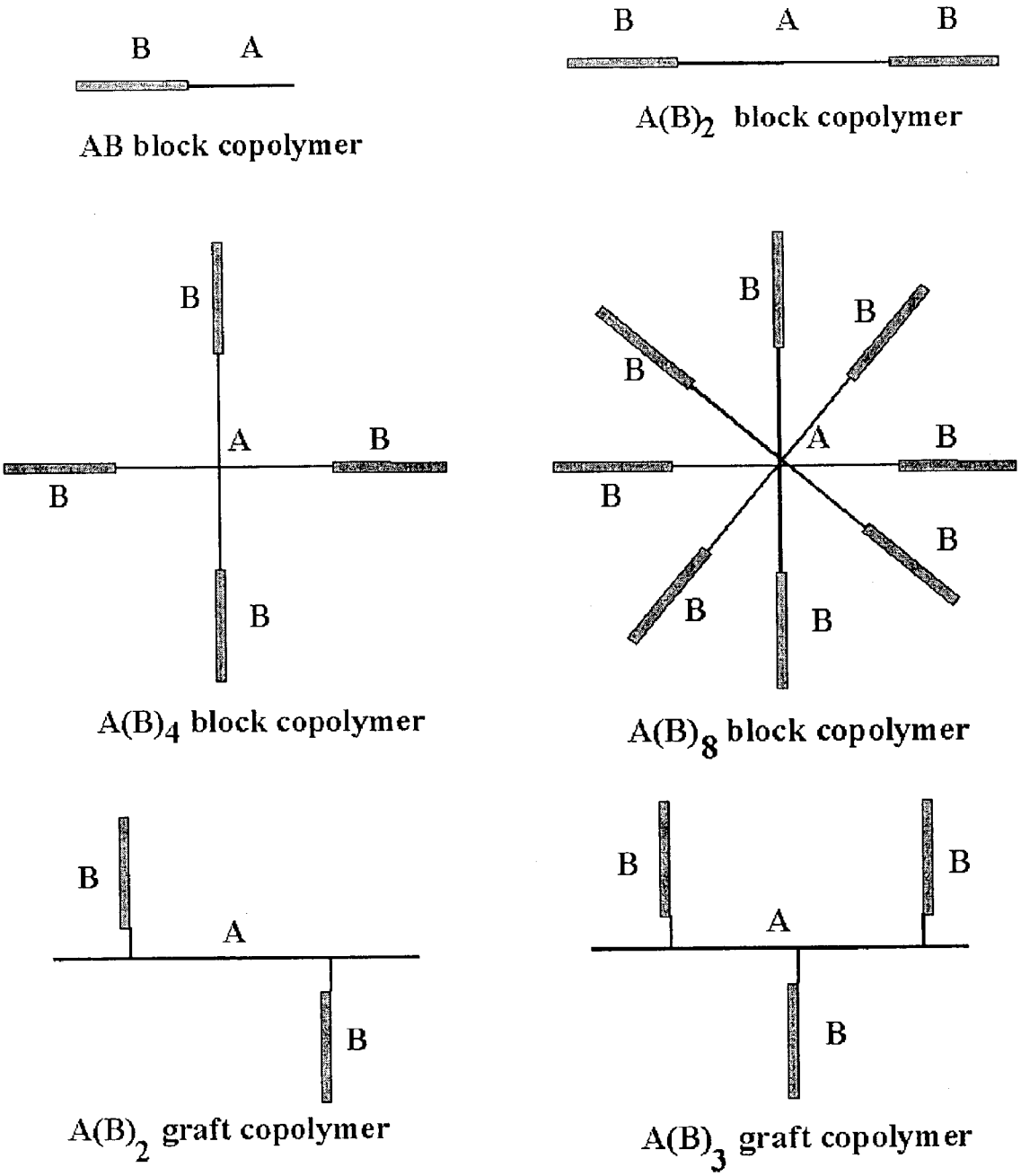
FIG. 1 is a schematic diagram of block copolymer architectures $A(B)_2$, $A(B)_4$ and $A(B)_8$, and graft copolymer architectures $A(B)_2$ and $A(B)_3$, according to the invention, shown here for comparison purposes with polymer AB.

According to one embodiment, the inventive copolymer readily dissolves in water at room temperature to form a low viscosity solution, but becomes a gel at a temperature just below body temperature. The copolymer contains an unresponsive core (A) to which a varying number of environment-responsive arms (B) are attached. Thus, the copolymer has a general structure $A(B)_n$. The arms (B) can be attached at any point along the core (A), provided the arms are accessible to the arms of other molecules for intermolecular aggregation upon changes in environmental conditions. For example, the arms may be attached to the ends of the core, thus forming a block copolymer, or may be attached along the chain of the core, thus forming a graft copolymer. FIG. 1 diagrammatically illustrates two-arm, four-arm and eight-arm block copolymer structures $A(B)_2$, $A(B)_4$ and $A(B)_8$, and graft copolymer structures $A(B)_2$, $A(B)_3$, with comparison to structure AB.

The core (A) may be a homopolymer or a copolymer, either linear or branched, and is chosen so that the core (A) itself is soluble in the selected solvent over the range of environmental conditions of interest. The arms (B) are chosen such that B itself would switch between being soluble and insoluble in the selected solvent between the environmental conditions of interest. When the core and arms are incorporated into a copolymer of structure $A(B)_n$, the copolymer is soluble in the selected solvent in conditions under which the arms are soluble. However, when an environmental condition is changed to a condition under which the arms (B) themselves would be insoluble, the B component of the copolymer precipitates to form aggregated domains with B components of adjacent copolymers. The aggregated B components are linked by A segments since B and A components are covalently linked within a copolymer molecule. Thus, a three-dimensional gel structure is formed containing many A segments connected via physical crosslinks of B aggregated domains.

In the resulting gel, the inventive copolymer incorporates an equilibrium quantity of solvent due to the compatibility between core A and the solvent, thereby forming a solvent-containing gel.

According to one embodiment of the invention, PEG is used as core A, poly(N-isopropyl acrylamide) (PNIPAAm), a temperature responsive polymer, is used for arms B. Copolymers are formed with varying numbers of PNIPAAm arms. These copolymers are water soluble at room temperature, forming low viscosity liquid aqueous solutions. However, upon heating, the copolymers rapidly and reversibly form strong gels (in less than a minute), exhibiting little syneresis.

The gelable composition according to the invention may contain mixtures of A(B)n copolymers that contain different A components, different B components, or have different n, or any combination thereof. In this way, mixtures can be used to optimize gelation kinetics or to achieve gel properties desirable for a particular application.

The Core. The core (A) is chosen such that, on its own, the core (A) is soluble in the selected solvent over the range of environmental conditions of interest. Thus, the core may be selected from homopolymers, or the core may itself be a copolymer (random, block or graft), either linear or branched, provided that A is soluble over the range of environmental conditions of interest.

Core (A) may either be provided as a stable compound or as a degradable compound. In the case where the core is degradable, the copolymer or copolymer composition degrades over time under appropriate conditions. For example, if the core is biodegradable in a physiological system, eventually the polymer structure will break down, resulting in release of the arms, and ultimately removal of the copolymer structure from the physiological system.

A number of possible cores (A) can be used according to the invention. The core may be selected from any synthetic, natural or biological polymers, including but not limited to polyethylene glycol (PEG) of varying molecular weights and degrees of branching, polyvinyl pyrrolidone, polyvinyl alcohol, polyhydroxyethylmethacrylate, and hyaluronic acid. Optionally, the core can have reactive groups at a variety of positions along or within its structure.

The Arms. The arms (B) are chosen such that B itself converts between being soluble and insoluble in the selected solvent when exposed to the environmental condition of interest.

The arms B may be selected according to an environment responsiveness suited to the intended application of the invention. For example, for in situ clinical applications, water-solubility under ambient conditions and aggregation under physiologic conditions is a desirable property of B. The environmental condition triggering the switch between ambient and physiological conditions may be selected from, but is not limited to, temperature, pH, ionic strength, and combinations thereof.

A number of choices for the arms (B) of the copolymer exist, including, but not limited to poly-N-isopropyl acrylamide (PNIPAAm), which is a temperature responsive polymer, hydroxypropylmethyl cellulose and other methyl cellulose derivatives, poly(ethylene glycol vinyl ether-co-butyl vinyl ether), polymers of N-alky acrylamide derivatives, poty(amino acid)s or peptide sequences such as silk and elastin peptides, poly(methacryloy L-alanine methyl ester), poly(methacryloy L-alanine ethyl ester). Nitrocellulose may be used as arms (B), for example when ethanol is used as solvent. Nitrocellulose in ethanol is known to form gel upon warming (Newman et al., J. Phys. Chem. 60:648–656, 1955). In the selection of arms (B), one of skill in the art would also consider whether the selected arms allow formation of a copolymer with the desired properties, which could easily be determined by observing the properties.

Arms (B) may be formed from a copolymer, for example a copolymer of vinyl ether of ethylene glycol and butyl vinyl ether, which may be used in an aqueous solvent system. For a copolymer, the LCST beyond which a polymer changes solubility, depends on the mole ratio of the constituent components. In the examples given by Kudaibergenov et al. (Macromol. Rapid. Commun, 16: 855–860, 1995), the LCST values range from 20° C. to 90° C. over a mole ratio range of 72:28 to 95:5.

Arms (B) may be formed from poly(methacryloyl-DL-alanine methyl ester) or derivatives thereof. In the paper by Ding et al. (Radiat. Phys. Chem., 42 (4–6): 959–962, 1993), the LCST of the examples given are between 20° C. to 40° C. The gel swells at low temperature (i.e., 0° C.) and starts to de-swell upon warming to 20° C. or above.

Further, the arms (B) may be formed of methyl cellulose or derivatives thereof. Depending on specifics of the chemical composition, especially the degree of methylation, methyl cellulose and its derivatives were report to have a LCST in the range of 40° C. to 70° C. (Nishimura et al., Macromol. Symp., 120: 303–313, 1997).

The arms (B) may be attached to the unresponsive core (A) at any location on the core, as long as the arms remain accessible to the arms of adjacent copolymer molecules, as part of the inventive composition. This structure allows for intermolecular aggregation of arms (B) when the environmental condition is altered such that B itself would become insoluble in the selected solvent. For example, arms B may be positioned at the ends of the core, thus forming a block copolymer, or along the chain of the core thus forming graft copolymers.

As used herein, the structure "A(B)n" denotes a copolymer having arms (B) positioned on the core (A) in any manner, so as to form a block or graft copolymer. Arms (B) may be located at one or more ends of A, forming a block or star copolymer configuration, or may be located along the length of the core, thereby forming a graft copolymer, with B positioned as "brushes" along the core, or may be positioned randomly along the core, provided the arms are accessible for aggregation with the arms of adjacent molecules.

Further, as the structure "A(B)n" is understood to mean that A and B are present in the specified ratio within a given molecule, but that the covalent bond between A and B may also comprise an additional component, resulting in A and B being covalently linked through such an additional component. An example wherein the additional component is a reactive spacer is described in more detail below.

The number of arms (B) attached to the core (A) is selected such that n of A(B)n is a number which is larger than, but not equal to one. For any given copolymer molecule, n is an integer greater than 1. Thus, the ratio of arms to core in the architecture of any given copolymer molecule is 2:1, (n=2) or greater. For example, the ratio of arms to core can be 4:1 (n=4) or 8:1 (n=8). The number of arms is not limited, provided that core is of adequate size to accommodate the selected number of arms, while still allowing the arms of one copolymer molecule to access the arms of an adjacent copolymer molecule when in solution. The selection of the number of arms may also depend on the desired properties of the gel, for example, to achieve a stronger or weaker gel, the number of arms may be adjusted.

The gelable composition formed according to the invention may be comprised of a plurality of different copolymers. Taking into account the proportions of different copolymer architectures within the composition, an average A(B)n can be determined for the composition. In this case, the average n ($n_{avg}$) must be greater than 1, but non-integer values of $n_{avg}$ are possible for any particular gelable composition. For example if the composition contains a mixture of copolymers of varying architectures, such as 50% copolymer AB and 50% copolymer A(B)$_2$, the $n_{avg}$ of the composition is 1.5. In the inventive composition, $n_{avg}>1$, taking into account all forms of A(B)n copolymers in the composition. For any individual copolymer molecule within the composition, n is an integer number, as described above. In compositions which contain a mixture of copolymers, it is possible to have a gel-forming composition comprising some copolymer molecules with n=1, some with n=4, etc. In order for such a composition to be gelable according to the invention, $n_{avg}$ should be adequately greater than 1, so that enough copolymer molecules with n>1 are present in the composition to allow formation of the gel network. In this way, copolymer molecules having the structure AB (n=1), which would not ordinarily form a gel with other AB copolymers, can become part of the gel network by having their single arm segment incorporated into the aggregates formed by the molecules having n>1.

Reactive Spacers. Reactive spacers "C" may be present between core A and arms B, thereby forming a copolymer of the generic structure A(CB)n. It is understood that A(CB)n is a variant or embodiment of A(B)n, as the structure A(B)n is understood to mean that A and B must be present in the specified ratio, but that the covalent bond between A and B may also comprise an additional component, resulting in A and B being covalently linked through component C.

Figure 2:
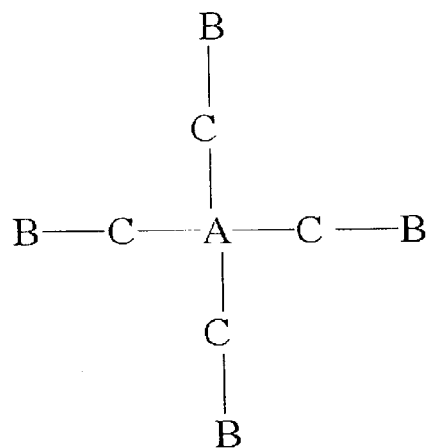
FIG. 2 is a schematic diagram of copolymer architectures $A(CB)_2$ and $A(CB)_4$ according to the invention.

FIG. 2 illustrates two-arm and four-arm copolymer structures with reactive spacers C. As can be seen in FIG. 2, when a reactive spacer C is present between A and B, the basic structure of A(B)n is met, and merely includes an additional component C within the covalent bonds binding A to B. In the embodiment of A(CB)n, two covalent bonds bind A to B, specifically, the bond between A and C, and the bond between C and B.

Reactive spacers C may be incorporated to allow cleavage of the copolymer, for such purposes as for rendering the copolymer degradable under desired conditions. Reactive spacer C may degrade via any suitable reaction, including but not limited to chemical reactions, biochemical reactions, enzymatic degradation, or photo-induced reactions. In the case where a reaction of the reactive spacers results in cleavage of the copolymer, as C degrades, A(CB)n is split into individual A and B components. In the context of a physiological application, if core A and arms B are of low enough molecular weight, they can be cleared from the site and removed from the body via renal clearance.

Biologically Active Molecules. A biologically active molecule may be included in the invention either through covalent attachment of the molecule to the structure of the copolymer or by including the molecule in a copolymer composition. In the case where the biologically active molecule is included in the copolymer composition, but not incorporated into the copolymer itself, the biologically active molecule is optimally selected from those having some degree of solubility in the desired solvent.

According to an embodiment wherein the biologically active molecule D is attached to the copolymer, it may be bound to either the core (A) or the arms (B) in such a way that the attachment allows release of the biologically active molecule D from the copolymer. For example, a covalent attachment of D to A may occur via a degradable spacer, such as C, described above.

As with the introduction of reactive spacer (C) in the copolymer, introduction of biologically active molecule D, with or without spacer C, is considered an embodiment of A(B)n. It is understood that D may be covalently attached to either A or B, and a copolymer polymer so formed would meet the requirement structure of A(B)n. The structure A(B)n is understood to mean that A and B must be present in the specified ratio, but that the covalent bond between A and B may also comprise an additional component such as D, through which the covalent attachment of A and B, may be indirectly achieved.

According to a further embodiment of the invention, biologically active components may be included in the polymeric composition formed according to the invention, but without any covalent link to the polymer itself. Advantageously, when a gel is formed, a biologically active compound present in the polymeric solution becomes trapped in the gel structure. This arrangement is conducive to slow release of the biologically active molecule from the gel structure within a physiological environment.

A biologically active molecule for incorporation into the copolymer or copolymer composition may be any which causes a physiological change or effect, such as a low molecular weight compound, drug, antibody, growth factor, peptide, oligonucleotide, genetic sequence, or compounds that modulate cell behaviours such as adhesion, proliferation or metabolism. A biologically active molecule may be attached to the copolymer or included in the copolymer composition in order to promote the viability or proliferation of cells encapsulated in such gels, or to influence the production of compounds by such cells.

The Solvent. Various solvents may be used with the copolymer composition. The solvent may be aqueous, including water, sodium chloride solutions such as physiological saline, cell culture media, or any medium that approximates a biological. system, such as extracellular matrix. The pH, and tonicity of a solvent may be any which allows adjustment as appropriate, so that the environmental condition can be adjusted within the copolymer composition in order for the composition to take on a gel form. Non-aqueous solvents may be used, or combination solvents including a polar organic and an aqueous component. For example, an alcohol may be used as the solvent, with or without water. Ethanol, methanol, isopropyl alcohol and other alcohols may be used as a solvent. Other polar organic solvents may be used alone or in combination with water. Non-polar organic solvents may be used with appropriate copolymers, such that A is soluble in the solvent, and B is soluble under certain environmental conditions and insoluble under other environmental conditions.

The term "solvent" may also refer to any prepared mixture of components which may include proteins, growth factors, buffers, ions, and other co-solutes. For example, culture media and extra cellular solutions contain water in combination with a number of co-solutes which are considered part of the solvent. Further, other soluble components, such as polymers may be included in the solvent. Such polymers may, for example, be synthetic polymers or copolymers that do not aggregate with the copolymer having A(B)n architecture. The solvent may contain, for example, the polymer used as core component (A) in the copolymer A(B)n. When such a polymer or copolymer is included in the solvent, it would not be considered in the calculation of navg unless it had a structure A(B)n and was capable of aggregation with arms B of the inventive copolymer. As an example of solvents which include polymers, PEG homopolymer and others may be included in the solvent.

Regardless of the solvent selected for use with the invention, the core (A) is selected to be soluble in the solvent over a range of environmental conditions of interest. The arms (B) are environment-responsive components which are soluble in the solvent under one set of environmental conditions, and which become insoluble in the solvent under different environmental conditions of interest.

Within the composition, the copolymer can be present in the solvent at any concentration that allows gelation to occur, for example a level of from about 5% to about 50% by weight, or from about 10% to about 25% by weight. This concentration depends on the nature of the solvent and the copolymer.

Additional Applications of the Invention. The invention may be used as described above, or as described herein below. The invention may be used for either physiological or industrial applications. Physiological and clinical applications of the invention include, but are not limited to, delivery of biologically active molecules, tissue and biomedical engineering, and therapeutics. Industrial applications of the invention include but are not limited to synthetic processes requiring timed release of reactive components, or as barriers.

The invention can be applied to delivery of biologically active molecules, for example but not limited to in vitro formation of drug delivery systems, in situ drug delivery, in situ gene delivery. The inventive polymer may be used to form drug delivery systems in vitro, which could then be implanted into a physiological region of a subject. Drug delivery systems may be formed in situ by suspending drug-containing particles in the copolymer composition, then injecting the composition into, or applying the composition onto specified sites of a subject causing gel formation to occur in vivo. Genes may be delivered in vivo using the inventive polymers and compositions. Gene delivery systems in situ can be formed by suspending gene-containing vesicles in the polymer solutions, then injecting the solutions into, or applying the solutions onto specified sites of patients causing gel formation to occur in vivo. Possible sites for implantation for in vitro formed systems or for insertion of in situ forming systems of biologically active molecules include but are not limited to periodontal cavities, intramuscular sites, subcutaneous sites, tumors, bones, joints, intraocular sites, sites that have been exposed by surgery, and wound sites.

The process for forming an in vitro implant may additionally involve maintaining the composition at least at a gelling temperature prior to insertion of said implant into a subject, so that the implant does not convert back to a liquid state.

For compositions having an LCST between ambient temperature and body temperature, the environmental condition that triggers gel formation is heating to body temperature. Thus, inserting the composition into the body causes the biologically active molecule to be trapped in the gel at the site of application, and sustained release from the site would then result.

Further, the invention may be used for in vitro or in situ encapsulation of cells. For encapsulation of cells in vitro, cells can be grown in incubation medium to which the copolymer is added when desirable, so as to keep cells in suspension under certain environmental conditions, but to retain them in a gel when environmental conditions are changed. Encapsulation of cells may also occur in situ by suspending cells in the copolymer composition under conditions at which the composition is a liquid (for example, below LCST), then injecting the composition into, or applying the composition onto specified sites of patients causing gel formation to occur in vivo. The sites for in situ injection of suspended cells in the composition, or for insertion of an in vitro formed implant of encapsulated cells can be selected from, but are not limited to, periodontal cavities, intramuscular sites, subcutaneous sites, tumors, bones, joints, intraocular sites, sites that have been exposed by surgery, and wound sites.

For applications involving encapsulated cells, the length of chain segments between the physical crosslinks of the copolymer may be selected such that the mesh size between crosslinks provides the appropriate molecular weight cut-off to provide immunoisolation of the encapsulated cells from the intended host while allowing the diffusion of desired nutrients to the cell, and the release of desired agents from the encapsulated cells to the host. In an application of in situ forming cell-containing gels, the copolymer would be soluble in water at ambient conditions (ie. room temperature), and the composition including suspended cells is injected into or applied onto a patient at the desired site. Body temperature triggers gel formation, thus causing the cells to be trapped in the gel at the site of injection or application. Cell proliferation and secretion of desired substances from the cell may then occur.

In cell-containing applications, it may be particularly advantageous to incorporate into the gel peptides or growth factors that promote cell adhesion, cell proliferation or otherwise influence cell metabolism in the desired manner. Such compounds may either be covalently linked to the copolymer, or incorporated in solid particles or liquid droplets that are co-encapsulated in the composition with the cells.

The composition may be used as a coating, barrier, sealant, filling or blocker of an anatomical structure or region, formed either in situ, or formed in vitro and implanted to an appropriate region. The composition may be positioned within a biological structure or on top of a biological structure. For example, the composition may be sprayed onto a wound site to provide a protective coating for the wound. It may also be injected into a blood vessel to block blood flow in that vessel. Such an application may be useful upstream of a tumor to block blood flow to the tumor. It may also be used as a temporary sealant during surgery.

For physiological applications of the composition according to the invention, it is advantageous that the gelation is reversible. For example, an implant placed in a subject in situ can be reversed by liquifying the implant, such as by localized cooling of the area in which the implant was applied. Applying a cold compress, ice, or using other methods of localized cooling could be used to effect liquification of the composition from a gel state.

Industrial (non-physiological) applications of the invention include separation processes, chemical synthetic processes requiring timed or environmentally cued release, or for partitioning of reactants. For example, a reactant in an aqueous reaction may be encapsulated within the composition in gel form (ie. at a temperature above LCST). When the reaction is cooled below LCST, the encapsulated reactants are released due to the phase change of the composition from gel to liquid, thereby releasing the encapsulated reactant to the reaction. Thermocycling reactions which require accurately timed additions of a reactant can incorporate the reactant in the inventive composition to ensure accurate release of a reactant at a particular temperature. In other industrial applications, the copolymer composition can provides a barrier, coating, blockage, sealing or filling. The gelation of the composition formed according to the invention is advantageously reversible over a number of cycles. This reversibility allows repeated gelation and liquification cycles.

EXAMPLES

Examples of the invention are presented below to illustrate the invention, but not to limit the scope of the invention.

Reagent Preparation and Handling. Reagents used throughout the examples are described below, along with appropriate storage requirements.

$Ce^{4+}$ Solutions (0.4 M) are prepared by directly dissolving solid ceric ammonium nitrate $Ce(NO_3)_6(NH4)_2$ in distilled deionized water. The solution is either prepared fresh everyday, or if it is to be stored for a short duration, it is first sonicated to remove dissolved oxygen, then placed in a tightly capped high density polyethylene (HDPE) or polypropylene (PP) bottle, and stored at 5° C.

NaOH solution (1 N) is prepared from 10 N NaOH by dilution with distilled deionized water. The prepared solution is stored in a HDPE bottle.

N-isopropyl acrylamide (NIPAAm) monomer of 99% purity stabilized with 0.1% methoxyhydroquinone (MHQ), purchased from ACROS Organics, is further purified before use. The three major impurities are acrylamide monomer, MHQ and acrylic acid. They are removed by recrystalization followed by ion-exchange processes. NIPAAm monomer is first dissolved in 50/50 heptane/toluene solvent at 60° C. slightly above the melting point of NIPAAm. The warm solution is filtered through 0.8 μm nylon membrane to eliminate undissolved impurities. The warm aliquot is then put into an ice bath to recrystalize NIPAAm monomer. The NIPAAm crystal is recovered by vacuum filtration. The recrystalization process is repeated twice to eliminate MHQ and residual acrylamide monomers. The solid is then dissolved in distilled deionized water as a 20 wt % solution. The solution is poured into a bed of anionic exchange resin (IRA-402, Cl form, SUPELCO) to eliminate trace amount of acrylic acid. The anion-free NIPAAm solution is separated from the resin by vacuum suction. The high purity NIPAAm monomer is then recovered by freeze-drying at −55° C., and under a vacuum below $10^{-4}$ bar.

OH-terminated PEG is selected and obtained as follows. Polyethylene glycol of various architectures and with varying number of chain ends terminated by reactive hydroxyl groups are purchased from Shearwater Polymers, Inc. They are used without further purification or modification.

The composition of the standard extracellular solution (formulated for beta-cell lines) was as follows: NaCl (140 mM), KCl (4 mM), $MgCl_2$ (1 mM), $CaCl_2$ (2 mM), and HEPES (10 mM). The final pH of 7.3 was achieved by adjusting with NaOH.

F-12K Nutrient Mixture (Kaighn's Modification) made by GibcoBRL was used as the cell culture media referred to herein as F-12K. Purified collagen used in any methods herein was Vitrogen™, obtained from Cohesion Technologies Inc., Palo Alto, Calif.

Example 1

Two-Armed Block Copolymer
PNIPAAm-PEG-PNIPAAm

Linear polyethylene glycol (MW 5077) with terminal hydroxyl groups at both ends of the chain, $HO(CH_2CH_2O)_{113}H$, was purchased from Shearwater Polymer (product name Sunbright DKH-50H, Lot. 68559) and used without further treatment. This reagent is herein referred to as the two-armed PEG.

The two-armed PEG (1.0 g) was mixed with 1.35 g of purified NIPAAm, dissolved in water, then mixed with 2.0 ml of a 0.4 M $Ce^{4+}$ solution, and 0.8 ml of 1N NaOH solution. The total mixture was 15 ml in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a helium blanket. The reaction vial was made of polypropylene instead of glass to avoid $Ce^{4+}$/OH-glass side reaction, which could lead to an increased production of PNIPAAm homopolymer. The product of this reaction is predominantly a tri-block copolymer consisting of a central segment of PEG, with two separate segments of PNIPAAm covalently attached to either end of the PEG segment.

The unreacted NIPAAm, PEG and residual Ceric salts, and PNIPAAm homopolymer were removed by dialysis using an ester cellulose membrane (Fisher Scientific) in a water bath for four weeks. The water was changed every 24 hours. The copolymer was recovered from the solution by high vacuum freeze-drying at −55° C., A 10 wt % sample was prepared by dissolving one gram of the tri-block polymer in 9.0 ml of cold water at 5° C. Below 30° C., the solution was colorless and transparent. Between 5° C. to 25° C., the solution was low in viscosity and thus could be easily drawn into a syringe through a 25 gauge needle. Upon heating to above 32° C., the solution became opaque immediately, and the entire 10 mL solution turned into a solid white gel in less than two minutes. The gel occupied the entire solution volume. The gel showed some elasticity, and could hold its own shape even when the sample vial was inverted. Storage at 37° C. resulted in slight shrinkage of the gel (10% in 24 hours, 20% in two months). Differential scanning calorimetry measurements of the sample showed an endothermic first order transition temperature at 33.1° C. The width at half peak height was 2.2° C. The phase transition observed was completely reversible over many cycles.

Example 2

Four Armed Block Copolymer PEG-(PNIPAAm)$_4$

Four-arm branched polyethylene glycol (MW 10486) with one terminal hydroxyl group at each branch was purchased from Shearwater Polymer (product name Sunbright PTE10000, Lot. 76606) and used without further treatment. This reagent is herein referred to as the 4-armed PEG.

The four-armed PEG (1.0 g) was mixed with 1.35 g of purified NIPAAm, dissolved in water, then mixed with 2.0 ml of a 0.4 M $Ce^{4+}$ solution, and 0.8 ml of 1N NaOH solution. The total mixture was 15 mL in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a helium blanket. The reaction vial was made of polypropylene instead of glass to avoid $Ce^{4+}$/OH-glass side reaction, which could lead to an increased production of PNIPAAm homopolymer. The product of this reaction is predominantly a branched copolymer consisting of a central four-armed PEG, and individual PNIPAAm segments covalently attached to the end of each arm of the four-armed PEG.

The unreacted NIPAAm, PEG and residual Ceric salt, and PNIPAAm homopolymer were removed by dialysis using an ester cellulose membrane [Fisher Scientific] in a water bath for four weeks. The water was changed every 24 hours. The copolymer is recovered from the solution by high vacuum freeze-drying at −55° C.

A 10% wt sample was prepared by dissolving one gram of the four-armed copolymer in 9.0 ml of 5° C. cold water. Below 30° C., the solution was colorless and transparent. Between 5° C. to 25° C., the solution was low in viscosity and thus could be easily drawn into syringe through a 25 gauge needle. Upon heating to above 32° C., the solution became opaque immediately, and the entire 10 mL solution quickly turned into a solid white gel in less than two minutes. The gel occupied the entire solution volume. The gel showed some elasticity. It could hold its own shape even when the sample vial was inverted. The gel was cohesively strong enough to be picked up by a pair of tweezers, and was stronger than the gel formed according to Example 1. Storage at 37° C. resulted in negligible shrinkage (less than 5% in two months). Differential scanning calorimetry measurements of the sample showed an endothermic first order transition temperature at 32.6° C. The width at half peak height was 3.4° C. The phase transition observed was completely reversible over many cycles.

Example 3

Eight Armed Block Copolymer PEG-(PNIPAAm)$_8$

Eight-arm branched polyethylene glycol (MW 19770) with a terminal hydroxyl group at each branch was purchased from Shearwater Polymer (product name Sunbright HGEO20000, Lot. 7D543) and used without further treatment. This reagent is herein referred to as the 8-armed PEG.

The eight-armed PEG (1.0 g) was mixed with 1.35 g of purified NIPAAm, dissolved in water, then mixed with 2.0 ml of a 0.4 M Ce$^{4+}$ solution, and 0.8 ml of 1N NaOH solution. The total mixture was 15 mL in volume. The reagents were cold mixed at 5° C. and sonicated to eliminate dissolved gas. The reaction was then allowed to proceed at 30° C. for 24 hours. At the end of 24 hours, the mixture was diluted to 100 ml by adding cold distilled water and placed in a 5° C. refrigerator to quench the reaction. The entire reaction was carried out under a Helium blanket. The reaction vial was made of polypropylene instead of glass to avoid Ce$^{4+}$/OH-glass side reaction, which can lead to an increased production of PNIPAAm homopolymer. The product of this reaction is predominantly a branched copolymer consisting of a central block of the eight-armed PEG, and eight separate segments of PNIPAAm covalently attached to the end of each arm of the eight-armed PEG.

The unreacted NIPAAm, PEG and residual Ceric salt, and PNIPAAm homopolymer were removed by dialysis using ester cellulose membrane [Fisher Scientific] in a water bath for four weeks. The water was changed every 24 hours. The copolymer is recovered from the solution by high vacuum freeze-drying at −55° C.

A 10 wt % sample was prepared by dissolved one gram of the eight-armed copolymer product in 9.0 ml of cold water at 5° C. Below 30° C., the solution was colorless and transparent. Between 5° C. to 25° C., the solution was low in viscosity and thus could be easily drawn into syringe through a 25 gauge needle. Upon heating above 32° C., the solution became opaque immediately, and the entire 10 mL solution quickly turned into a solid white gel in less than two minutes. The gel occupied the entire solution volume. The gel showed some elasticity. It could hold its own shape even when the sample vial was inverted. The gel was cohesively strong enough to be picked up by a pair of tweezers, and was stronger than the gel formed according to Example 1, and comparable in strength to the gel of Example 2.

Storage at 37° C. resulted in negligible gel shrinkage (less than 5% in two months). Differential scanning calorimetry measurements of the sample showed an endothermic first order transition temperature at 33.5° C. The width at half peak height was 2.8° C. The phase transition observed was completely reversible over many cycles.

Example 4

Synthesis, Purification and Thermal Characteristics of 50/50 Copolymers of PEG/PNIPAAm having Architecture A(B)$_2$, A(B)$_4$ and A(B)$_8$ The copolymers were synthesized by Ce$^{4+}$/OH redox initiated free radical polymerization in water. Four hydroxyl-terminated PEGs were purchased from Shearwater and used without further purification: monomethoxy-PEG of 2,000 Da (i.e., 1 arm of length 2,000 Da), linear PEG diol of 4,600 Da (i.e., 2 arm PEG with each arm length of 2,300 Da), 4 arm star PEG of 9,300 Da (arm length=2,325 Da), and 8 arm star PEG of 19,700 Da (arm length=2,460 Da). All functionalized PEGs have polydispersity indices of less than 1.04.

The following exemplary conditions and procedure may be used for batch synthesis of PEG-PNIPAAm copolymers having architecture A(B)$_2$, A(B)$_4$ and A(B)$_8$, shown for comparison purposes with AB. The reaction solution volume is 30 ml in all cases. No NaOH is added to the reaction solution. The solvent is distilled water, and the reaction temperature is 30° C. The reagents are cold mixed at 5° C., and then sonicated for 10 to 20 minutes to eliminate dissolved oxygen. Subsequently, the mixture is subjected to an inert gas surge for 5 minutes to pre-saturate the solution with Helium gas. The reaction is then allowed to proceed for 24 hours under a water-saturated Helium blanket. The reaction vessel is made of Teflon (or polypropylene) instead of glass to avoid Ce$^{4+}$/OH-glass side reaction, which could lead to an increased production of homopolymer. At the end of 24 hours, the mixture was diluted to 100 ml by adding cold distilled water and placed in a 5° C. refrigerator to quench the reaction. The detailed reaction conditions are summarized in Table 1.

TABLE 1

Conditions for Batch Synthesis of 50/50 PEG/PNIPAAm Copolymers

| Structure | Reaction Temp. (° C.) | Reaction volume (ml) | Reaction Duration (hr) | 0.4 M Ce$^{4+}$ vol. (ml) | NIPAAm mass (g) | PEG mass (g) | PEG/ NIPAAm feed ratio | PEG/PNIPAAm final composition |
|---|---|---|---|---|---|---|---|---|
| AB | 30 | 30 | 24 | 8.0 | 1.0 | 3.0 | 75/25 | 49/51 |
| A(B)$_2$ | 30 | 30 | 24 | 8.0 | 0.81 | 1.5 | 65/35 | 48/52 |

TABLE 1-continued

Conditions for Batch Synthesis of 50/50 PEG/PNIPAAm Copolymers

| Structure | Reaction Temp. (° C.) | Reaction volume (ml) | Reaction Duration (hr) | 0.4 M Ce$^{4+}$ vol. (ml) | NIPAAm mass (g) | PEG mass (g) | PEG/ NIPAAm feed ratio | PEG/PNIPAAm final composition |
|---|---|---|---|---|---|---|---|---|
| A(B)$_4$ | 30 | 30 | 24 | 8.0 | 0.87 | 1.2 | 58/42 | 51/49 |
| A(B)$_8$ | 30 | 30 | 24 | 8.0 | 0.79 | 1.0 | 56/44 | 49/51 |

The copolymers were purified by dialysis. Cellulose ester membrane of various molecular weight cut-off [Fisher Scientific] were selected for such purpose. The details of purification conditions are provided in Table 2, including the molecular weight cut off (MWCO) of dialysis tubes used, and the recovered yield calculated as (dry copolymer)/(initial PEG mass+initial monomer mass).

TABLE 2

Conditions for Purification of 50/50 PEG/PNIPAAm Copolymers

| Copolymers | MWCO of Tube | Dialysis Time | Recovered Yield (wt %) |
|---|---|---|---|
| AB | 3,500 | 4 weeks | 15~25% |
| A(B)$_2$ | 8,000 | 4 weeks | 20~30% |
| A(B)$_4$ | 15,000 | 4 weeks | 20~30% |
| A(B)$_8$ | 25,000 | 4 weeks | 15~25% |

The copolymer molecular weights were determined by proton NMR [Varian Unity Plus 500 MHz]. The ratio of the methyl protons in isopropyl groups to the methylene protons of PEGs was used to determine the ratio of NIPAAm to ethylene glycol repeat units. Using the known molecular weight of PEG, the molecular weight of PNIPAAm segments, and thus the copolymer molecular weight can be deduced. The composition and characteristics of copolymers formed are given in Table 3.

TABLE 3

Composition and Characteristics of Copolymers

| Structure | "A" Block Weight[a] (Da) | PEG MW per Arm (Da) | "B" Block Weight (Da)[b,c] | PEG/ PNIAAm (by weight) | Total Molecular Weight(Da)[c] |
|---|---|---|---|---|---|
| AB | 2,000 | 2,000 | 2,100 ± 200 | 49/51 | 4,100 ± 200 |
| A(B)$_2$ | 4,600 | 2,300 | 2,500 ± 200 | 48/52 | 9,600 ± 400 |
| A(B)$_4$ | 9,300 | 2,330 | 2,200 ± 200 | 51/49 | 18,200 ± 800 |
| A(B)$_8$ | 19,700 | 2,460 | 2,600 ± 200 | 49/51 | 40,000 ± 1,600 |

[a]As reported by manufacturer; polydispersity of 1.04 or better.
[b]Average from three synthesis batches
[c]As calculated from NMR analysis The thermal characteristics of the copolymers were determined by differential scanning calorimetry (DSC) [TA2010, TA Instrument]. DSC scans of aqueous solutions of each copolymer at various concentrations were taken at a heating rate of 2° C./minute. Transition temperatures, both onset of thermal transitions ($T_{onset}$) and peak temperature of endotherm ($T_{max}$), and the enthalpy of thermal transition normalized to PNIPAAm content, $\Delta H$ (J/g of PNIPAAm), were determined. The results are tabulated in Tables 4 to 7 for copolymers, and in Table 8 for solutions of PNIPAAm homopolymer (comparative example) in water. The measurement precision for temperature is ±0.2° C. and enthalpy is ±2 J/g for all cases.

TABLE 4

DSC Results for
1 arm 50/50 PEG/PNIPAAm Copolymer AB (Comparative Example)

| Concentration | $T_{onset}$(° C.) | $T_{max}$(° C.) | $\Delta H$(J/g of PNIPAAm) |
|---|---|---|---|
| 20% | 27.3 | 28.7 | 30 |
| 15% | 28.7 | 29.8 | 32 |
| 10% | 30.0 | 31.0 | 35 |

TABLE 5

DSC Results for 2 arm 50/50 PEG/PNIPAAm Copolymer A(B)$_2$

| Concentration | $T_{onset}$(° C.) | $T_{max}$(° C.) | $\Delta H$(J/g of PNIPAAm) |
|---|---|---|---|
| 20% | 26.4 | 28.5 | 29 |
| 15% | 28.6 | 30.0 | 36 |
| 10% | 30.0 | 31.0 | 38 |

TABLE 6

DSC Results for 4 arm 50/50 PEG/PNIPAAm Copolymer A(B)$_4$

| Concentration | $T_{onset}$(° C.) | $T_{max}$(° C.) | $\Delta H$(J/g of PNIPAAm) |
|---|---|---|---|
| 20% | 26.2 | 29.3 | 29 |
| 15% | 29.4 | 30.9 | 34 |
| 10% | 30.2 | 31.4 | 37 |

TABLE 7

DSC Results for 8 arm 50/50 PEG/PNIPAAm Copolymer A(B)$_8$

| Concentration | $T_{onset}$ | $T_{max}$ | ΔH(J/g of PNIPAAm) |
|---|---|---|---|
| 20% | 28.2 | 30.3 | 28 |
| 15% | 29.7 | 31.1 | 33 |
| 10% | 30.8 | 32.0 | 34 |

TABLE 8

DSC Results for PNIPAAm homopolymer (Comparative Example)

| Concentration | $T_{onset}$(° C.) | $T_{max}$(° C.) | ΔH(J/g of PNIPAAm) |
|---|---|---|---|
| 10% | 32.6 | 33.6 | 43 |
| 7.5% | 32.8 | 33.7 | 44 |
| 5% | 32.7 | 33.4 | 45 |

The results show that the transition temperature is concentration dependent. As concentration decreases, the transition temperature rises slightly. The range of onset temperature is between 26° C. to 31° C. for all four types of copolymers, which is a suitable range for a physiological application requiring a liquid state at an ambient temperature and a gel state at a physiological temperature. The range of ΔH values illustrates that the copolymer molecular architecture influences the phase transition of the PNIPAAm segments, while the comparison between the copolymers and the homopolymer suggests that the presence of PEG may have prevented PNIPAAm segments from fully collapsing. The enthalpy of gelation for copolymers according to the invention are about 15% to 35% lower than that of PNIPAAm homopolymer (see Table 8) measured at the equal PNIPAAm content.

Example 5

Rheological Properties and Gelation Mechanism of Block and Star Copolymers of PEG and PNIPAAm of Varying Architectures Block or star copolymers with a central hydrophilic polyethylene glycol (PEG) segment as core (A), and temperature responsive poly(N-isopropylacrylamide) (PNIPAAm) terminal segments as arms (B) of various architectures A(B)$_2$, A(B)$_4$ and A(B)$_8$, were synthesized to investigate the structures and properties relationship. A comparative copolymer having the structure AB is also evaluated. The synthesis and purification of copolymers were conducted according to the schemes given in Example 4. The compositions of the copolymers are identical to those given in Example 4 (see Table 3, Composition and Characteristics of Copolymers). All four copolymers evaluated herein are of approximately 50/50 PEG/PNIPAAm ratio by weight.

At 5° C., the viscosities of 20% wt solutions were between 700 to 950 cP, and they could be easily injected through a 25G needle. Upon warming to body temperature, A(B)$_2$, A(B)$_4$ and A(B)$_8$ formed a strong associative network gel with aggregates of PNIPAAm segments acting as physical crosslinks, whereas AB formed a weaker gel by micellar packing and entanglement. The values of elastic modulus, loss tangent, and yield strength were between 1300 to 2600 Pa, 0.4 to 0.6, and 300 to 1000 Pa, respectively.

The mechanical and rheological properties of the copolymers were characterized using a temperature controlled rheometer [Carri-Med, TA Instrument] with a cone and plate (4 cm diameter, 2 degree angle) geometry. Yield stress ($\sigma_c$), critical strain ($\gamma_c$), and elastic and loss moduli (G', G") were determined under oscillatory mode at 37° C. Solution viscosities were measured under flow mode at 5° C. using 20 wt % copolymer solutions in water.

Figure 3:
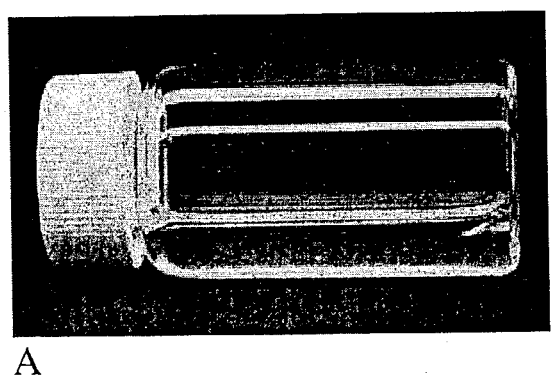
FIG. 3 illustrates an $A(B)_4$ polymer of PEG and PNIPAAm in aqueous solution. Picture A illustrates a 20% wt $A(B)_4$ solution at 25° C., while picture B illustrates a 20% wt $A(B)_4$ gel at 37° C.
Figure 3:
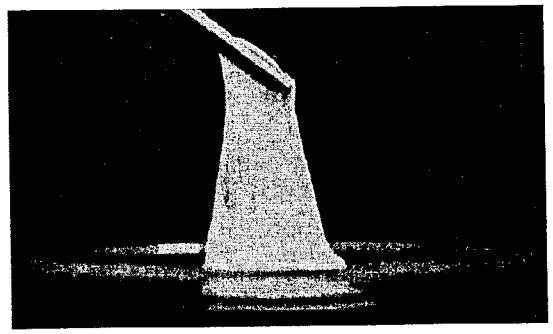

FIG. 3 illustrates a composition according to the invention comprising the A(B)$_4$ polymer of PEG and PNIPAAm in aqueous solution at a concentration of 20% by weight. As shown in picture A, the composition is a liquid at room temperature (25° C.), and forms a strong gel at body temperature (37° C.), as shown in picture B.

Figure 4:
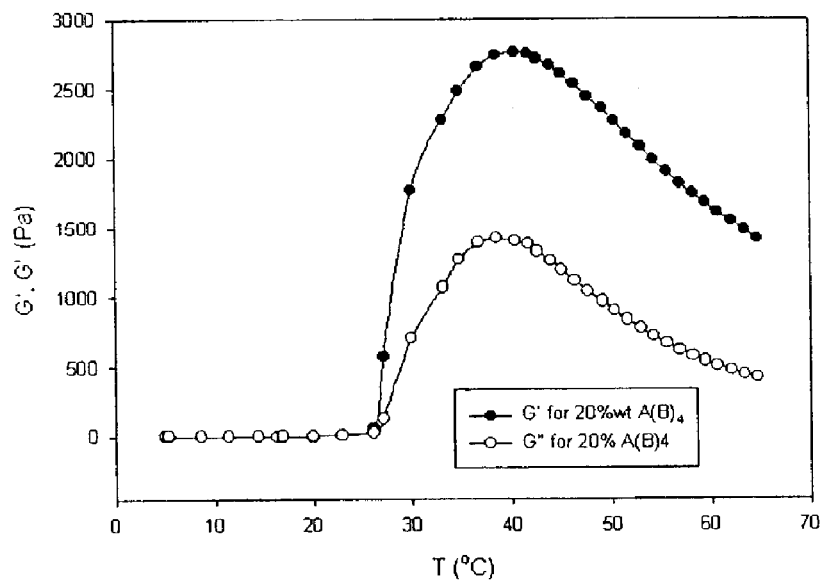
FIG. 4 illustrates that for a 20% solution of $A(B)_4$ the onset of increase in the elastic and loss moduli, shown as (A)
Figure 4:
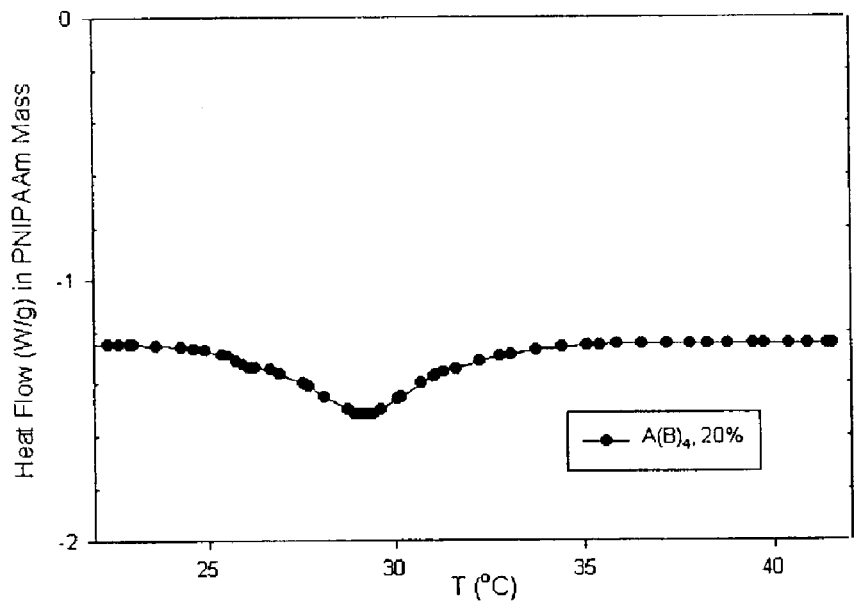

FIG. 4 illustrates that for a 20% solution of A(B)$_4$, the onset of both elastic and loss modulus, shown as (A) temperature sweep of oscillatory measurement, is between the onset and the peak temperatures in the endotherm as detected by (B) DSC temperature scan. When PNIPAAm collapses at an elevated temperature, heat is evolved, and measured by DSC. The endotherm of a DSC scan is corresponding to the molecular event of PNIPAAm segments collapsing. The synchronization of the endotherm and moduli onset temperatures illustrates that the thermal transitions are linked to the mechanical changes, and therefore the aggregation measured by the thermal transitions are at least partially intermolecular in nature. It is known that the mechanical strength (i.e., modulus) is scale to the number of crosslinks per unit volume. The higher the crosslink density, the higher the modulus will be. The inter-aggregation will lead to connection between molecules (i.e., forming physical crosslinks) which ultimately gives rise to a high mechanical strength; whereas, intra-aggregation will produce no physical crosslinks, thus no drastic rise of modulus is expected upon transition temperature. The rapid rise of modulus at the onset of endotherm illustrates a gelation mechanism of network formation for the multiple arm copolymers.

FIG. 5 shows the superposition of DSC scans for multiple cycles at 2° C./min, for aqueous compositions comprising either (A) the eight-armed polymer A(B)$_8$ or (B) the four-armed polymer A(B)$_4$, both at a concentration of 20% wt in water. All samples were subjected to cyclic heating and cooling for up to 30 cycles. The thermal behaviour of the material is completely reversible. There was a small hysteresis of 2° C. observed between heating and cooling curves.

The superposability of the scans indicates that the gelation process is completely reversible. Although the enthalpy of gel melting is identical to the enthalpy of gel formation, at a heating/cooling rate of 2° C./min, there is a difference between the peak temperatures of the heating endotherm and the cooling exotherm of about 2° C. in the scans shown in FIG. 5. The difference can be attributed to the kinetics of gelation process. At infinitely slow cooling/heating rates, the two peak temperatures should be identical. Another thermoreversible polymer hydroxypropylmethyl cellulose (HPC) has been reported to have a temperature lag of 8 to 10° C. at a much slower heating rate of 0.25° C./min (Sarkar, Journal of Applied Polymer Science, 24: 1073–1087, 1979). The relatively small temperature hysteresis seen with these copolymers is indicative of rapid gelation kinetics compared to that of cellulose derivatives.

FIG. 6 illustrates the theological behavior of copolymers at body temperatures. The viscoelastic and mechanical properties were evaluated by subjecting the gels at 37° C. to oscillatory stresses ($\sigma$) that ranged from 0.1 to 3,000 Pa at 1 Hz frequency, and measuring the resulting strains ($\gamma$). The elastic modulus (G'), loss modulus(G"), overall modulus $(G^*=[G'^2+G''^2]^{1/2})$ and loss tangent, (tan $\delta$=G"/G') were then calculated.

The elastic modulus of $A(B)_2$, $A(B)_4$ and $A(B)_8$ copolymers are between 1,300 to 2,600 Pa, which makes them "hard gels", and tan delta values are between 0.4 to 0.7, which indicate that they are very much "solid-like". The examples provided in FIG. 6 are compositions of $A(B)_2$, $A(B)_4$ and $A(B)_8$ copolymers at 20% wt in water. A rheological scan of the one-arm copolymer (AB) composition (20% wt in water) is also provided as a comparative example. Multiple arm copolymers in general have a higher modulus than a single arm copolymer. A higher modulus means a higher number of load bearing chains per unit volume; and that is believed to be due to the very nature of having multiple aggregation blocks in one molecule. A one-arm copolymer is also different from the multiple arm copolymers in terms of its yielding behavior. Passing the yield point, the tan delta increases as stress increases, whereas the multiple arm copolymers behave otherwise. This behavior suggests a different gelation mechanism. For compositions comprising 20% wt copolymer in water, $A(B)_4$ showed the highest modulus and highest yield stress, and is thus the strongest material among the four polymers prepared.

FIG. 6, part A and B show that for all four gels, G' and G* (respectively) are approximately constant over a wide range of oscillatory stress values, then decrease sharply at high stress. The stress at which the decrease occurs is different among the four gels.

Table 9 provides a summary of the constant G' and G" values at linear-viscoelastic region, which shows that G' and G" increase as the number of arms increase from 1 to 2 to 4, but then decrease upon further branching to an 8 arm architecture. The G', G" values shown in Table 9 were measured at $\omega$=1 Hz, and $\sigma$=50 Pa which is within the linear viscoelastic region of all the materials above. Values are the averages from three synthesis batches. Accordingly, loss tangent for all four gels is also seen to be approximately constant over a wide range of oscillatory stress values, but then deviate from linearity at high stress, as illustrated in FIG. 6, part C. The yield point is defined as where overall modulus, G*, deviates from linearity as illustrated in FIG. 6, part B. The corresponding stress and strain are called critical yield stress and strain.

parison of the theological results for the two-, four- and eight-arm structures shows that the elastic and loss moduli in the linear viscoelastic region, as well as the yield stress and strain are all highest for the four-arm structure, indicating that the four-arm copolymer forms gels that are highest in strength, as well as deformability. Branching should have two effects on gel rheology. Increasing the number of arms should increase the degree of crosslinking in the gel via the covalent linkage of arms; hence gel strength should increase. However, as the number of arms increases, aggregation between PNIPAAm blocks within the same molecule becomes increasingly favored over inter-molecular aggregation. Since intramolecular aggregation does not contribute to physical crosslinking, degree of physical crosslinking would decrease as branching increases beyond a certain point. The maximum in gel strength observed for the 4-arm gel may thus be explained by the counterbalancing effects of covalent crosslinking and physical crosslinking. It is also interesting to note that the loss tangent increases monotonically from 0.40 to 0.53 to 0.62 as the degree of branching increases from two to eight arms, indicating that the relative viscous component increases with the degree of branching.

A comparison of the theological behavior of the one-arm micellar aggregate gels to the multi-arm physically crosslinked gels shows that the most striking difference between the two classes of gels is that the loss tangent decreases at high stress for the one-arm gel while for all the other gels, loss tangent increases at high stress. The contrast in trends is suggestive of a fundamental difference in the gel structure. The viscous component of the one-arm gel becomes increasingly dominant at high values of oscillatory stress, while the elastic component of the multi-arm gels become increasingly dominant.

The one-arm gel shows a significantly lower values of G' than the multi-arm gels. According to Hvidt's classification, (Hvidt, et al., Journal of Physical Chemistry, 98:12320–12328, 1994; Almgren, W Brown, S. Hvidt, Colloid and Polymer Science, 273:2, 1995), the one arm gel would be considered a "soft gel" (i.e., G'<1,000 Pa), while the others would be considered "hard gels" (i.e., G'>1,000 Pa). In contrast to the low modulus, the one arm gel has the highest critical strain among the gels, and a relatively high yield stress, lower than only the four-arm gel. With only one end tethered to PNIPAAm aggregates, PEG segments in one arm gels are more freely mobile and more readily deform-

TABLE 9

Gel Strength of Copolymers at 37° C.

| Materials | G', G" at linear viscoelastic region | | Loss tan | $\sigma_c$, Yield | $\gamma_c$, Critical |
|---|---|---|---|---|---|
| | G'(Pa) | G"(Pa) | G"/G' | Stress(Pa) | Yield Strain |
| AB | 630 ± 130 | 180 ± 30 | 0.28 ± 0.03 | 750 ± 90 | 1.10 ± 0.15 |
| $A(B)_2$ | 2100 ± 200 | 850 ± 80 | 0.40 ± 0.04 | 600 ± 70 | 0.30 ± 0.03 |
| $A(B)_4$ | 2600 ± 250 | 1400 ± 150 | 0.53 ± 0.04 | 1000 ± 150 | 0.37 ± 0.04 |
| $A(B)_8$ | 1300 ± 150 | 800 ± 90 | 0.62 ± 0.04 | 300 ± 50 | 0.22 ± 0.03 |

The gelation mechanism suggests that multiple PNIPAAm segments are required in the same molecule in order for physically crosslinked hydrogel networks to be formed. Thus it is expected that the two-, four-, and eight-arm structures would form gels via a physical crosslinking mechanism, while the one-arm diblock copolymer would form a gel via the micellelar aggregation mechanism. Comable than PEG segments in multi-arm gels that are tethered at both ends. The low modulus and high critical strain of one-arm gel are a reflection of the ease of deformability. Likewise, with only one end sterically shielded by PNIPAAm aggregates, the free end of PEG segments in one-arm gels are allowed to interact with other PEG segments and form entanglements. The relatively high yield stress of one-arm gels may be the result of significant entanglement of PEG corona.

The viscosity of PEG-PNIPAAm copolymer solutions was measured at 5° C., and for a shear rate range of 0.1 to 200 $s^{-1}$. For a shear rate greater than 5 $s^{-1}$, all solutions are essentially Newtonian. The viscosity for 20% wt a one-arm diblock, two-arm triblock, four-arm star and eight-arm star are 750 cP, 950 cP, 900 cP and 700 cP respectively. All these solutions are of low enough viscosity to easily inject through a 25G needle.

This example illustrates that block and star copolymers of PEG and PNIPAAm form liquid aqueous solutions at low temperature, and transform to relatively strong elastic gels upon heating. Multiple arm copolymers form gels via a physical crosslinking mechanism, while diblock copolymers gel by a micellar aggregation mechanism. The rheological properties of the gels are dependent on the molecular architecture, with $A(B)_4$ showed optimal properties (i.e., at 20% wt). The copolymer compositions according to the invention show relatively low injection viscosities and high gel strengths, and are therefore useful for clinical and physiological applications such as in situ drug delivery, cell encapsulation and anatomical barriers.

Example 6

Toxicity of Eight-Arm PEG/PNIPAAm Copolymer

The toxicity of a the eight-arm copolymer of PEG and PNIPPAm was tested in F-12K culture media using HIT insulinoma cells (INS-1). Solutions having 1%, and 3% concentrations of the eight-arm copolymer in culture medium were tested. F-12K culture medium included 10% fetal bovine serum. The control (0%) solution was prepared as F-12K culture medium (with 10% fetal bovine serum), but without copolymer. Multi-well plates (0.5 mL/well) were seeded with HIT cells, and either a copolymer-containing solution or the control culture medium. The wells were examined for cell viability up to 50 hours.

These dilute copolymer solutions showed no effect on cell viability in terms of % dead cells and total number of live cells compared to the control medium. The eight-arm PEG-PNIPAAm copolymer illustrated compatibility with the HIT insulinoma cells for incubations up to 50 hours. The copolymer was evaluated for toxicity at low level concentrations in culture medium so that all copolymer molecules would be freely accessible to cells. Cells would be less exposed to the polymer molecules when in gel form (ie at higher copolymer concentrations) and it would be expected that cell toxicity of the gel form of the polymer would be considerably less than that of the dissolved form of the polymer.

Example 7

Gelation Phase Conversion for PEG/PNIPAAm Copolymer Compositions

The copolymer compositions prepared according to the invention take on a gel form at different temperatures depending on a number of parameters. A four-arm copolymer prepared according to Example 4 was examined for gelation in different solvents.

Gelation phase diagram observations were made using both a visual method and an inverted tube method. The gelation temperature is defined to be the temperature at which the composition (polymer/solvent mixture) becomes completely opaque.

Further, the inverted tube method was used to assess gelation point. Using a 1.4 cm round diameter tube, a composition is defined to be in the gel state if it does not flow after the tube has been inverted for 10 seconds. The gelation temperatures determined using the visual end point and inverted tube methods were identical.

For cell culture media or extracellular solution media, at polymer concentrations of less than about 14 wt %, compositions became turbid suspensions of white solid particles upon heating that flow easily instead of gelling. Thus, at concentrations lower than 14 weight percent, compositions of polymers in these media do not form gels. In water, no gel forms below 6 wt % polymer, and in 157 mM saline solution, no gel forms below 7 wt % polymer.

The gelation temperature increases as the concentration of copolymer in the composition decreases. Standard extracellular solution depresses the LCST. The polymer is less viscous in this solvent compared to the other solvents tested.

FIG. 7 shows the phase diagrams of compositions comprising the copolymer in different solvents: (a) water, (b) physiological NaCl (157 mM), (c) F-12K Media, and (d) standard extracellular solution. The diagrams show temperature/concentration conditions at which the compositions (polymer/solvent mixtures) exist as solutions or gels, as well as the minimum concentration required for gel formation to occur. These data illustrate that the nature of the solvent affects the temperature at which a gel forms. A variety of different concentrations shown in the phase diagram would be appropriate for clinical and/or physiological applications of the composition.

Example 8

Copolymer of Nitrocellulose

A copolymer according to the invention is formed using nitrocellulose as arms (B) and PEG as core (A). A copolymer having either $A(B)_4$ or $A(B)_8$ architecture is formed. A gelable composition according to the invention comprises dilution of the nitrocellulose/PEG copolymer in ethanol at a concentration of about 10%.

Nitrocellulose in ethanol forms a gel upon warming. The gelation temperature depends on molecular weight and concentration. For a molecular weight of 197,000, the gelation temperature is 10° C., 5.5° C. and −20° C. for a polymer fraction of 0.5%, 1% and 4% respectively, and the theta temperature was found to be 301–310 K (Newman et al., J. Phys. Chem. 60:648–656, 1955).

Example 9

Composition Comprising Different Copolymers

A composition according to the invention is formed using copolymers having AB and $A(B)_4$ architecture, as described above in Example 4. The composition comprises a total of 15 wt % copolymer in physiological saline. The proportion of AB to $A(B)_4$ in the composition is 2:3, resulting in an average n value ($n_{avg}$) of 2.8 (or 14/5). The resulting composition is liquid at ambient temperature, and converts to a gel when injected into a subcutaneous site of a subject. This change from liquid to gel is due to a change in environmental condition, specifically the change from ambient temperature to body temperature.

Example 10

Composition Comprising Different Copolymers

A composition according to the invention is formed using a graft copolymer having A'(B)$_3$ architecture and a block copolymer having A"(B)$_4$ architecture, as described above in Example 4. In this case A' differs from A". Each A is a PEG of differing molecular weight. However, B is the same (PNIPAAM) for both types of copolymer. The composition comprises a total of 13 wt % copolymer in cell culture media. The proportion of A'(B)$_3$ to A"(B)$_4$ in the composition is 10:3, resulting in an average n value ($n_{avg}$) of 3.23. The resulting composition is liquid at ambient temperature, and converts to a gel at a temperature below body temperature.

Example 11

Thermoreversible Gel Composition

A thermoreversible gel (TRG) was prepared and purified as follows. As used herein, thermoreversible gel is synonymous with the term thermally reversible gel.

Synthesis of TRG. TRG synthesis conditions were as follows. Polyethylene glycol (PEG, 2.42 g), N-isopropyl acrylamide (NiPAAm, 1.75 g) and degassed endotoxin-free distilled water (44 ml) were measured and transferred to a 100 mL glass, round-bottom reaction flask. The reactor was flushed with nitrogen gas and placed in a 50° C. water bath for at least 15 minutes. A ceric ammonium nitrate solution in nitric acid (0.6370 g in 6 ml IM HNO$_3$) is then added to the reactor via syringe. The reaction proceeded for 3 hr after the addition of the cerium solution. After 3 hr, 50 mL of degassed endotoxin-free water 4° C. was added to the reactor and the reaction vessel was placed in an ice bath for 15 minutes to dissolve the synthesized TRG.

As compared with Example 1, the increase in reaction temperature to 50° C. from 30° C. and the addition of nitric acid were adopted to increase cerium initiation activity and polymerization rate allowing for reduced reaction times (3 hr from 24 hr). In addition, the amount of ceric salt added was also reduced (5.5 fold) making removal of residual cerium contamination from the synthesized gel simpler.

TRG Purification. The purification method used previously in Example 1(dialysis) was replaced by an extraction technique. This modification was driven by the need for a faster, scaleable method to produce large quantities of pure TRG useful for product applications. The extraction technique involves incubating the dry gel reaction product (after cerium removal) in warm water (50–60° C.) at low concentration (5–10% wt/vol) for 24 hr to remove water-soluble extractables. The solid, swollen TRG was then filtered and rinsed with warm water. The extractions may be repeated as many times as necessary to attain a constant TRG composition (as determined by NMR spectroscopy), normally 2–4 extractions. This simple, relatively fast and effective technique reduced purification time from ~3 weeks to ~1 week.

FIG. 9 shows the effective removal of impurities detected by gel permeation chromatography resulting from extraction.

By way of comparison, the thermoreversible gel produced in this example is now compared with a gel produced according to a typical gel (or copolymer) produced according to Example 1.

Table 9 illustrates material differences between a "modified" gel formed according to this example ("modified"), and one prepared according to Example 1 ("original"). The amount of PEG incorporated into the modified copolymer, as determined by NMR spectroscopy, was increased from 6 to 12 mol % relative to the original copolymer. However, little change in the gelation temperature was observed, indicating that this parameter is not particularly sensitive to TRG composition. Conversely, the solution and rheological properties of the TRG were highly dependent on composition. The modified TRG (in 20 wt % solutions) gives lower viscosity solutions making them more easily injected through high gauge needles. In addition, the modified TRG formed softer gels on heating, as indicated by the reduced G' values in comparison to the original TRG. In general, both the original and modified TRG may be classed as a weak hydrogel above the gelation temperature, with the modified TRG showing similar in mechanical properties to commercially available wrinkle-filling gels.

TABLE 9

Physicochemical property comparison of original and modified TRG

| Synthesis Method | PEG content (mol %) | Gel Temp. (° C.) | Viscosity (cP) | G' (Pa) | G" (Pa) | δ |
|---|---|---|---|---|---|---|
| Original | 6 | 32.9 | 1,500–15000 | 3000–5,000 | 1800–3,000 | 0.6 |
| Modified | 12 | 32.3 | 1,100–1,500 | 155–225 | 60–90 | 0.25–0.55 |

The above-described embodiments of the present invention are intended to be examples only. Alterations, modifications and variations may be effected to the particular embodiments by those of skill in the art without departing from the scope of the invention, which is defined solely by the claims appended hereto.

What is claimed is:

1. A method of forming a removable implant in an animal comprising inserting a thermally reversible gel into said animal, said gel having a semi-solid form at body temperature and a liquid form upon cooling to a temperature below a threshold temperature, said threshold temperature being at least 5° C. below body temperature, wherein said gel comprises a star copolymer and a solvent, the copolymer having the star-shaped structure A(B)n with n>2, wherein
   A is soluble in the solvent, and is selected from the group consisting of polyethylene glycol (PEG), polyvinyl pyrrolidone, polyvinyl alcohol, polyhydroxyethyl-methacrylate, and hyaluronic acid; and
   B is convertible between soluble and insoluble in the solvent when heated to a temperature between ambient temperature and body temperature, and comprises poly-N-isopropyl acrylamide (PNIPAAm), hydroxypropylmethyl cellulose and other methyl celluloses, poly(ethylene glycol vinyl ether-co-butyl vinyl ether), polymers of N-alkyl acrylamides, poly(amino acid)s, peptide sequences, poly(methacryloyl-L-alanine methyl ester), poly(methacryloyl-L-alanine ethyl ester) or nitrocellulose; and wherein said gel is reversibly convertible between said semi-solid and said liquid form as a function of temperature.

2. The method of claim 1 wherein the gel is liquefied, and thus re-shapeable, re-sizable, or removable at a temperature below the threshold temperature.

3. The method of claim 1 wherein the implant comprises a gel placed within the lumen of the vas deferens for birth control.

4. The method of claim 1 wherein the implant comprises a cervical seal for birth control.

5. The method of claim 1 wherein the implant comprises a wrinkle filler, a joint spacer, a tissue spacer, a tissue expander, a vessel blocker, a cosmetic enhancer, or a breast implant filler.

6. The method of claim 1, additionally comprising the step of removing the implant by cooling the body in the region of the implant to a temperature below the threshold temperature and extracting the implant.

7. A method of forming an in situ implant or an implant in vitro comprising the steps of:
   (i) forming a gelable composition comprising a star copolymer and an aqueous solvent, the copolymer having the star-shaped structure A(B)n with n>2, wherein
      A is soluble in the solvent, and is selected from the group consisting of polyethylene glycol (PEG), polyvinyl pyrrolidone, polyvinyl alcohol, polyhydroxyethylmethacrylate, and hyaluronic acid; and
      B is convertible from soluble to insoluble when heated to a temperature between ambient temperature and body temperature, and comprises poly-N-isopropyl acrylamide (PNIPAAm), hydroxypropylmethyl cellulose and other methyl celluloses, poly(ethylene glycol vinyl ether-co-butyl vinyl ether), polymers of N-alkyl acrylamides, poly(amino acid)s, peptide sequences, poly(methacryloyl-L-alanine methyl ester), poly(methacryloyl-L-alanine ethyl ester) or nitrocellulose;
      the composition being reversibly convertible from liquid to gel when B is insoluble; and
   (ii) inserting said composition into a subject to form an in situ implant or heating said composition to at least said gelling temperature to form an in vitro implant.

8. The method of claim 1, wherein A is selected from the group consisting of polyethylene glycol (PEG), polyvinyl pyrrolidone, and polyvinyl alcohol, polyhydroxyethylmethacrylate.

9. The method of claim 1, wherein A is PEG.

10. The method of claim 1, wherein B is PNIPAAm.

11. The method of claim 1, wherein the copolymer is present in the aqueous solution at a level of from 5 to 50% by weight.

12. The method of claim 1, wherein the copolymer is present in the aqueous solution at a level of from 10 to 25% by weight.

13. The method of claim 1, wherein the copolymer is present in the aqueous solution at a level of 20% by weight.

14. The method of claim 12, wherein the copolymer is present in the aqueous solution at a level of from 15 to 25% by weight.

* * * * *